(12) United States Patent
Shekdar

(10) Patent No.: US 11,680,265 B2
(45) Date of Patent: Jun. 20, 2023

(54) GENOME EDITING USING EFFECTOR OLIGONUCLEOTIDES FOR THERAPEUTIC TREATMENT

(71) Applicant: Research Foundation to Cure AIDS, Inc., Brooklyn, NY (US)

(72) Inventor: Kambiz Shekdar, New York, NY (US)

(73) Assignee: Research Foundation to Cure AIDS, Inc., Brooklyn, NY (US)

( * ) Notice: Subject to any disclaimer, the term of this patent is extended or adjusted under 35 U.S.C. 154(b) by 437 days.

(21) Appl. No.: 16/858,512

(22) Filed: Apr. 24, 2020

(65) Prior Publication Data

US 2020/0407727 A1 Dec. 31, 2020

Related U.S. Application Data

(62) Division of application No. 14/777,490, filed as application No. PCT/US2014/026787 on Mar. 13, 2014, now Pat. No. 10,669,547.

(60) Provisional application No. 61/867,522, filed on Aug. 19, 2013, provisional application No. 61/801,822, filed on Mar. 15, 2013.

(51) Int. Cl.
| | | |
|---|---|---|
| *A61K 48/00* | (2006.01) | |
| *C12N 15/113* | (2010.01) | |
| *C12N 15/10* | (2006.01) | |
| *C12Q 1/6876* | (2018.01) | |

(52) U.S. Cl.
CPC ........ *C12N 15/1138* (2013.01); *C12N 15/102* (2013.01); *C12Q 1/6876* (2013.01); *C12N 2310/152* (2013.01); *C12N 2310/3181* (2013.01); *C12N 2310/3231* (2013.01); *C12N 2310/333* (2013.01); *C12N 2310/336* (2013.01); *C12N 2310/533* (2013.01); *C12N 2330/50* (2013.01)

(58) Field of Classification Search
None
See application file for complete search history.

(56) References Cited

U.S. PATENT DOCUMENTS

| | | | |
|---|---|---|---|
| 6,057,102 | A | 5/2000 | Landau |
| 6,692,965 | B1 | 2/2004 | Shekdar |
| 8,309,356 | B2 | 11/2012 | Glazer |
| 10,669,547 | B2 | 6/2020 | Shekdar |
| 2005/0220772 | A1 | 10/2005 | Chow |
| 2006/0147937 | A1 | 7/2006 | Shekdar |
| 2009/0106853 | A1 | 4/2009 | Shekdar |
| 2009/0202496 | A1 | 8/2009 | Ghen |
| 2010/0172882 | A1 | 7/2010 | Glazer |
| 2010/0212040 | A1 | 8/2010 | Shekdar |
| 2011/0262406 | A1 | 10/2011 | Del Campo |
| 2011/0293585 | A1 | 12/2011 | Del Campo |
| 2012/0015841 | A1 | 1/2012 | Shekdar |
| 2016/0046948 | A1 | 2/2016 | Shekdar |
| 2020/0407727 | A1* | 12/2020 | Shekdar ............ C12N 15/1138 |

FOREIGN PATENT DOCUMENTS

| | | |
|---|---|---|
| WO | WO199313121 A1 | 7/1993 |
| WO | WO199419023 A1 | 9/1994 |
| WO | WO199532305 A1 | 11/1995 |
| WO | WO199855495 A2 | 12/1998 |
| WO | WO199855495 A3 | 5/1999 |
| WO | WO2009006336 A1 | 1/2009 |
| WO | WO2011133802 A1 | 10/2011 |

OTHER PUBLICATIONS

Allers, K. et al. (Mar. 10, 2011). "Evidence For The Cure Of HIV Infection By CCR5Δ32/Δ32 Stem Cell Transplantation," Blood 117(10):2791-2799.
Andrieu-Soler, C. et al. (2005, e-pub. Jul. 7, 2005). "Stable Transmission Of Targeted Gene Modification Using Single-Stranded Oligonucleotides With Flanking LNAs," Nuc. Acids Res. 33(12):3733-3742.
Bertoni, C. et al. (Dec. 2009, e-pub. Oct. 23, 2009). "Enhanced gene repair mediated by methyl-CpG-modified single-stranded oligonucleotides," Nucleic Acids Research 37(22):7468-7482.
Bonner, M. et al. (Apr. 3, 2012). "DNA Damage Response Pathway and Replication Fork Stress During Oligonucleotide Directed Gene Editing," Mol. Therapy Nucleic Acids 1:e18, 9 pages.
Chen, F. et al. (Sep. 2011, e-published on Jul. 17, 2011). "High-Frequency Genome Editing Using ssDNA Oligonucleotides With Zinc-Finger Nucleases," Nature Methods 8(9):753-755.
European Communication Pursuant to Article 94(3) EPC dated Aug. 23, 2017 for EP Application No. 14770615.4, filed on Sep. 9, 2015, 7 pages.
Extended European Search Report dated Sep. 30, 2016 for EP Application No. 14770615.4 filed on Mar. 13, 2014, 10 pages.
Hari, Y. et al. (2003). "Selective Recognition Of CG Interruption By 2', 4'-BNA Having 1-Isoquinolone As a Nucleobase In a Pyrimidine Motif Triplex Formation," Tetrahedron 59:5123-5128.
Hou, P. et al. (Aug. 9, 2013). "Pluripotent Stem Cells Induced From Mouse Somatic Cells By Small-Molecule Compounds," Science 341(6146):651-654.
Hyrup, B. et al. (Jan. 1996). "Peptide Nucleic Acids (PNA): Synthesis, Properties and Potential Applications," Bioorg. Med. Chem. 4(1):5-23.
Hütter, G. et al. (Feb. 12, 2009). "Long Term Control of HIV by CCR5 Delta32/ Delta32 Stem Cell Transplantation," The New England Journal of Medicine 360(7):692-698.
Imanishi, T. et al. (Aug. 21, 2002). "BNAs: Novel Nucleic Acid Analogs With a Bridged Sugar Moiety," Chem. Commun. (Camb) 21(16):1653-1659.
International Preliminary Report On Patentability, dated Sep. 15, 2015, for PCT Patent Application No. PCT/US2014/026787, filed on Mar. 13, 2014, 7 pages.

(Continued)

*Primary Examiner* — Michael D Burkhart
(74) *Attorney, Agent, or Firm* — Morrison & Foerster LLP

(57) ABSTRACT

The invention provides compositions and methods of making and using effector oligonucleotides, including effector oligonucleotides with greater than one mismatch as compared to its target sequence. These effector oligonucleotides are useful for improving the efficiency of genomic editing as well as providing therapeutic benefits to individuals in need thereof.

13 Claims, 7 Drawing Sheets

Specification includes a Sequence Listing.

(56) References Cited

OTHER PUBLICATIONS

International Search Report dated Jul. 30, 2014, for PCT Patent Application No. PCT/US2014/026787, filed on Mar. 13, 2014, 5 pages.

Kim, Y.C. et al. (May 19, 2009). "The Transcriptome Of Human CD34+ Hematopoietic Stem-Progenitor Cells," PNAS 106(20):8278-8283.

Lacoste, A. et al. (Sep. 4, 2009). "An Efficient and Reversible Transposable System For Gene Delivery and Lineage-Specific Differentiation In Human Embryonic Stem Cells," Cell Stem Cell 5(3):332-342.

Larsson, H.M. et al. (2012). "Sorting Live Stem Cells Based On Sox2 mRNA Expression," PLoS One 7(11):e49874, 8 pages.

Liu, X.L. et al. (Oct. 2007). "Differential Gene Expression In Human Hematopoietic Stem Cells Specified Toward Erythroid, Megakaryocytic, and Granulocytic Lineage," J. Leukoc. Biol. 82(4):986-1002.

Mali, P. et al. (Feb. 15, 2013, e-pub. Jan. 3, 2013). "RNA-Guided Human Genome Engineering via Cas9," Science 339(6121):823-826.

Mali, P. et al. (Feb. 15, 2013, e-pub. Jan. 3, 2013). "Supplementary Materials for RNA-guided Human Genome Engineering via Cas9," Science Express pp. 2-36, 36 pages.

Mcneer, N.A. et al. (Jun. 2013, e-pub. Oct. 18, 2012). "Systemic Delivery of Triplex-Forming PNA and Donor DNA by Nanoparticles Mediates Site-Specific Genome Editing of Human Hematopoietic Cells In Vivo," Gene Therapy 20(6):658-669.

Mitsuoka, Y. et al. (Mar. 2009). "A Bridged Nucleic Acid, 2',4'-BNACOC: Synthesis Of Fully Modified Oligonucleotides Bearing Thymine, 5-methylcytosine, Adenine and Guanine 2',4'-BNACOC Monomers and RNA-Selective Nucleic-Acid Recognition," Nuc. Acids Res. 37(4):1225-1238.

Orlando, S.J. et al. (Aug. 2010, e-pub, Jun. 8, 2010). "Zinc-finger Nuclease-Driven Targeted Integration Into Mammalian Genomes Using Donors With Limited Chromosomal Homology," Nucleic Acids Research 38(15):e152, 15 pages.

Rahman, S.M. et al. (2007). "Highly Stable Pyrimidine-Motif Triplex Formation At Physiological pH Values By a Bridged Nucleic Acid Analogue," Angew Chem. Int. Ed. Engl. 46(23):4306-4309.

Rahman, S.M.A. et al. (Apr. 9, 2008). "Design, Synthesis, and Properties of 2',4'-BNA(NC): A Bridged Nucleic Acid Analogue," J. Am. Chem. Soc. 130(14):4886-4896.

Sambrook, J. et al. (2001). Molecular Cloning: A Laboratory Manual, vol. 1, Cold Spring Harbor Laboratory Press, pp. 6.28-6.33.

Schleifman, E. et al. (Sep. 23, 2011). "Targeted Disruption of the CCR5 Gene in Human Hematopoietic Stem Cells Stimulated by Peptide Nucleic Acids," Chemistry & Biology 18(9):1189-1198.

Written Opinion of the International Searching Authority dated Jul. 30, 2014, for PCT Patent Application No. PCT/US2014/026787, filed on Mar. 13, 2014, 6 pages.

* cited by examiner

Figure 1

CCR5 Coding sequence ttggattatcaagtgtcaagtccaatctatgacatcaattattacatcggagccctgccaaaaat
caatgtgaagcaaatcgcagcccgcctcctgctccgtcactactggtgttcatctttggttttgt
gggcaacatgctggtcatcctcatcctgataaactgcaaaaggctgaagagcatgactgacacta
cctgctcaacctggccatctctgacctgtttttccttcttactgtccccttcggctcactatgctgcc
gcccagtgggactttggaaatacaatgtgtcaactcttgacagggctctatttttataggcttctctct
ggaatcttcttcatcatcctcctgacaatcgataggtacctggctgtcgtccatgctgtgtttgctttaa
aagccaggacggtcacctttgggggtggtgacaagtgtgatcacttgggtggtggctgtgttgcgt
ctctcccaggaatcatcttaccagatctcaaaagaaggtcttcattacacctgcagctctcatttc
catacagtcagtatcaattctggaagaatttccagacattaaagatagtcatcttgggctggtc
ctgccgctgcttgtcatgtcatctgctactcgggaatcctaaaaactctgcttcggtgtcgaaatga
gaagaaggcacaggctgtgaggcttatctgaaccatcatgatttattttctcttctggctcc
ctacaacattgtcctcctgaacaccttccagaattctttggcctgaataattcagtagtctaa
caggtttggaccaagctatgcaggtgacaggtgacagagactcttggggatgacgcactgctgcatcaaccc
atcatctatgccatcgtttgtcggggagaagttcagaaactcttagtctttcttccaaaagcacattgcc
aaacgcttctgcaaatgctgttctatttccagaagaggctcccgagcgaagcaagtcagtttaca
cccgatccactggggagcaggaaatatctgtgggcttgtga (SEQ ID NO:1)

Figure 2

WT CCR5 Protein Sequence

MDYQVSSPIYDINYYTSEPCQKINVKQIAARLLPPLYSLVFIFG
FVGNMLVILILINCKRLKSMTDIYLLNLAISDLFFLLTVPFWAH
YAAAQWDFGNTMCQLLTGLYFIGFFSGIFFIILLTIDRYLAVVH
AVFALKARTVTFGVVTSVITWVVAVFASLPGIIFTRSQKEGLH
YTCSSHFPYSQYQFWKNFQTLKIVILGLVLPLLVMVICYSG
ILKTLLRCRNEKKRHRAVRLIFTMIVYFLFWAPYNIVLL
NTFQEFFGLNNCSSSNRLDQAMQVTETLGMTHCCINPIY
AFVGEKFRNYLLVFFQKHIAKRFCKCCSIFQQEAPERASS
VYTRSTGEQEISVGL- (SEQ ID NO:2)

Figure 3

Δ32 CCR5 Protein Sequence

MDYQVSSPIYDINYYTSEPCQKINVKQIAARLLPPLYSLVFIFGFVGNMLVILILINCKRLKSMTDIYLLNLAISDLFFLLTVPFWAHYAAAQWDFGNTMCQLLTGLYFIGFFSGIFFIILLTIDRYLAVVHAVFALKARTVTFGVVTSVITWVVAVFASLPGIIFTRSQKEGLHYTCSSHFPYIKDSHLGAGPAAACHGHLLLGNPKNSASVSK- (SEQ ID NO:3)

Figure 4A

| Effector Oligonucleotide | | Sequence from 5' to 3' |
|---|---|---|
| Number | Name | |
| 1 | d32.T.40.40 | GAAGGTCTTCATTACACCTGCAGCTCTCATTTTCCATACATTAAAGATAGTCATCTTGGGGCTGGTCCTGCCGCTGCTTG (SEQ ID NO:5) |
| 2 | d32.B.40.40 | CAAGCAGCGGCAGGACCAGCCCCAAGATGACTATCTTTAATGTATGGAAAATGAGAGCTGCAGGTGTAATGAAGACCTTC (SEQ ID NO:6) |
| 3 | d32.T.40.60 | GAAGGTCTTCATTACACCTGCAGCTCTCATTTTCCATACATTAAAGATAGTCATCTTGGGCTGGTCCTGCCGCTGCTTGTC ATGGTCATCTGCTACTCG (SEQ ID NO:7) |
| 4 | d32.B.40.60 | CGAGTAGCAGATGACCATGACAAGCAGCGGCAGGACCAGCCCCAAGATGACTATCTTTAATGTATGGAAAATGAGAGCT GCAGGTGTAATGAAGACCTTC (SEQ ID NO:8) |
| 5 | d32.T.60.40 | TCTTTACCAGATCTCAAAAAGAAGGTCTTCATTACACCTGCAGCTCTCATTTTCCATACATTAAAGATAGTCATCTTGGGGC TGGTCCTGCCGCTGCTTG (SEQ ID NO:9) |
| 6 | d32.B.40.60 | CAAGCAGCGGCAGGACCAGCCCCAAGATGACTATCTTTAATGTATGGAAAATGAGAGCTGCAGGTGTAATGAAGACCTTC TTTTGAGATCTGGTAAAGA (SEQ ID NO:10) |
| 7 | d32.T.60.60 | TCTTTACCAGATCTCAAAAAGAAGGTCTTCATTACACCTGCAGCTCTCATTTTCCATACATTAAAGATAGTCATCTTGGGGC TGGTCCTGCCGCTGCTTGTCATGGTCATCTGCTACTCG (SEQ ID NO:11) |
| 8 | d32.B.60.60 | CGAGTAGCAGATGACCATGACAAGCAGCGGCAGGACCAGCCCCAAGATGACTATCTTTAATGTATGGAAAATGAGAGCT GCAGGTGTAATGAAGACCTTCTTTTGAGATCTGGTAAAGA (SEQ ID NO:12) |
| 9 | d32.T.125.125 | CTTTGGGGTGGTGACAAGTGTGATCATCACTTGGGTGGCTCTGCAGCTCTGCATTTCCATAGATAGTCATCTTGGGGCTGGTCCTGCCGCTGCT TGTCATGGTCATCTGCTACTCGGGAATCCTAAAAACTCTGCTTCGGTGTCGAAATGAGAGGCACAGGGCGTGTGA GGCTTAT (SEQ ID NO:13) |
| 10 | d32.B.125.125 | ATAAGCCTCACAGCCCTGTGCCTTCTTCTCATTTCGACACGAAGCAGAGTTTTAGGATTCCGAGTAGCAGATGACC ATGACAAGCAGCGGCAGGACCAGCCCCAAGATGACTATCTTTAATGTATGGAAAATGAGAGCTGCAGGTGTAATGAAGA CCTTCTTTTTGAGATCTGGTAAAGATGATTCCTGGGAGAGACGCAAACACAGCCACCAGTGATCACACTTGTCACC ACCCCAAAG (SEQ ID NO:14) |
| 19* | d32.T.60.60.s | TCTTTACCAGATCTCAAAAAGAAGGTCTTCATTACACCTGCAGCTCTCATTTTCCATACATTAAAGATAGTCATCTTGGGGC TGGTCCTGCCGCTGCTTGTCATGGTCATCTGCTACTCG (SEQ ID NO:15) |
| 20* | d32.B.60.60.s | CGAGTAGCAGATGACCATGACAAGCAGCGGCAGGACCAGCCCCAAGATGACTATCTTTAATGTATGGAAAATGAGAGCT GCAGGTGTAATGAAGACCTTCTTTTGAGATCTGGTAAAGA (SEQ ID NO:16) |

*Phosphorothioate linkages were used in the last 30 linkages on both ends of the effector oligonucleotide for 19 and 20

SEQUENCE LISTING

<160> NUMBER OF SEQ ID NOS: 60

<210> SEQ ID NO 1
<211> LENGTH: 1059
<212> TYPE: DNA

<213> ORGANISM: Homo sapiens

<400> SEQUENCE: 1

```
ttggattatc aagtgtcaag tccaatctat gacatcaatt attatacatc ggagccctgc      60
caaaaaatca atgtgaagca aatcgcagcc cgcctcctgc ctccgctcta ctcactggtg     120
ttcatctttg gttttgtggg caacatgctg gtcatcctca tcctgataaa ctgcaaaagg     180
ctgaagagca tgactgacat ctacctgctc aacctggcca tctctgacct gttttttcctt    240
cttactgtcc ccttctgggc tcactatgct gccgcccagt gggactttgg aaatacaatg     300
tgtcaactct tgacagggct ctattttata ggcttcttct ctggaatctt cttcatcatc     360
ctcctgacaa tcgataggta cctggctgtc gtccatgctg tgtttgcttt aaaagccagg     420
acggtcaccc ttggggtggt gacaagtgtg atcacttggg tggtggctgt gtttgcgtct     480
ctcccaggaa tcatctttac cagatctcaa aagaaggtc ttcattacac ctgcagctct     540
cattttccat acagtcagta tcaattctgg aagaatttcc agacattaaa gatagtcatc     600
ttggggctgg tcctgccgct gcttgtcatg gtcatctgct actcgggaat cctaaaaact     660
ctgcttcggt gtcgaaatga aagaagagg cacagggctg tgaggcttat cttcaccatc     720
atgattgttt attttctctt ctgggctccc tacaacattg tccttctcct gaacaccttc     780
caggaattct ttggcctgaa taattgcagt agctctaaca ggttggacca agctatgcag     840
gtgacagaga ctcttgggat gacgcactgc tgcatcaacc ccatcatcta tgcctttgtc     900
ggggagaagt tcagaaacta cctcttagtc ttcttccaaa agcacattgc caaacgcttc     960
tgcaaatgct gttctatttt ccagcaagag gctcccgagc gagcaagctc agtttacacc    1020
cgatccactg gggagcagga aatatctgtg ggcttgtga                           1059
```

<210> SEQ ID NO 2
<211> LENGTH: 352
<212> TYPE: PRT
<213> ORGANISM: Homo sapiens

<400> SEQUENCE: 2

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
```

```
                    165                 170                 175
Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
        210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
        290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 3
<211> LENGTH: 215
<212> TYPE: PRT
<213> ORGANISM: Artificial Sequence
<220> FEATURE:
<223> OTHER INFORMATION: Synthetic Construct

<400> SEQUENCE: 3

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ile Lys Asp Ser His Leu Gly Ala
```

```
                    180                 185                 190
Gly Pro Ala Ala Ala Cys His Gly His Leu Leu Leu Gly Asn Pro Lys
                195                 200                 205

Asn Ser Ala Ser Val Ser Lys
        210                 215

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
gtcagtatca attctggaag aatttccaga ca                                     32

<210> SEQ ID NO 5
<211> LENGTH: 80
<212> TYPE: DNA
<213> ORGANISM: Artificial Sequence
<220> FEATURE:
<223> OTHER INFORMATION: Synthetic Construct

<400> SEQUENCE: 5
gaaggtcttc attacacctg cagctctcat tttccataca ttaaagatag tcatcttggg       60
gctggtcctg ccgctgcttg                                                   80

<210> SEQ ID NO 6
<211> LENGTH: 80
<212> TYPE: DNA
<213> ORGANISM: Artificial Sequence
<220> FEATURE:
<223> OTHER INFORMATION: Synthetic Construct

<400> SEQUENCE: 6
caagcagcgg caggaccagc cccaagatga ctatctttaa tgtatggaaa atgagagctg       60
caggtgtaat gaagaccttc                                                   80

<210> SEQ ID NO 7
<211> LENGTH: 100
<212> TYPE: DNA
<213> ORGANISM: Artificial Sequence
<220> FEATURE:
<223> OTHER INFORMATION: Synthetic Construct

<400> SEQUENCE: 7
gaaggtcttc attacacctg cagctctcat tttccataca ttaaagatag tcatcttggg       60
gctggtcctg ccgctgcttg tcatggtcat ctgctactcg                            100

<210> SEQ ID NO 8
<211> LENGTH: 100
<212> TYPE: DNA
<213> ORGANISM: Artificial Sequence
<220> FEATURE:
<223> OTHER INFORMATION: Synthetic Construct

<400> SEQUENCE: 8
cgagtagcag atgaccatga caagcagcgg caggaccagc cccaagatga ctatctttaa       60
tgtatggaaa atgagagctg caggtgtaat gaagaccttc                            100

<210> SEQ ID NO 9
<211> LENGTH: 100
```

<212> TYPE: DNA
<213> ORGANISM: Artificial Sequence
<220> FEATURE:
<223> OTHER INFORMATION: Synthetic Construct

<400> SEQUENCE: 9
tctttaccag atctcaaaaa gaaggtcttc attacacctg cagctctcat tttccataca    60
ttaaagatag tcatcttggg gctggtcctg ccgctgcttg                          100

<210> SEQ ID NO 10
<211> LENGTH: 100
<212> TYPE: DNA
<213> ORGANISM: Artificial Sequence
<220> FEATURE:
<223> OTHER INFORMATION: Synthetic Construct

<400> SEQUENCE: 10
caagcagcgg caggaccagc cccaagatga ctatctttaa tgtatggaaa atgagagctg    60
caggtgtaat gaagaccttc ttttgagat ctggtaaaga                           100

<210> SEQ ID NO 11
<211> LENGTH: 120
<212> TYPE: DNA
<213> ORGANISM: Artificial Sequence
<220> FEATURE:
<223> OTHER INFORMATION: Synthetic Construct

<400> SEQUENCE: 11
tctttaccag atctcaaaaa gaaggtcttc attacacctg cagctctcat tttccataca    60
ttaaagatag tcatcttggg gctggtcctg ccgctgcttg tcatggtcat ctgctactcg   120

<210> SEQ ID NO 12
<211> LENGTH: 120
<212> TYPE: DNA
<213> ORGANISM: Artificial Sequence
<220> FEATURE:
<223> OTHER INFORMATION: Synthetic Construct

<400> SEQUENCE: 12
cgagtagcag atgaccatga caagcagcgg caggaccagc cccaagatga ctatctttaa    60
tgtatggaaa atgagagctg caggtgtaat gaagaccttc ttttgagat ctggtaaaga   120

<210> SEQ ID NO 13
<211> LENGTH: 250
<212> TYPE: DNA
<213> ORGANISM: Artificial Sequence
<220> FEATURE:
<223> OTHER INFORMATION: Synthetic Construct

<400> SEQUENCE: 13
ctttggggtg gtgacaagtg tgatcacttg ggtggtggct gtgtttgcgt ctctcccagg    60
aatcatcttt accagatctc aaaaagaagg tcttcattac acctgcagct ctcatttttcc  120 atacattaaa gatagtcatc ttggggctgg tcctgccgct gcttgtcatg gtcatctgct  180
actcgggaat cctaaaaact ctgcttcggt gtcgaaatga aagaagagg cacagggctg   240 tgaggcttat                                                          250

<210> SEQ ID NO 14
<211> LENGTH: 250
<212> TYPE: DNA
<213> ORGANISM: Artificial Sequence
<220> FEATURE:

<223> OTHER INFORMATION: Synthetic Construct

<400> SEQUENCE: 14
ataagcctca cagccctgtg cctcttcttc tcatttcgac accgaagcag agtttttagg    60
attcccgagt agcagatgac catgacaagc agcggcagga ccagcccaa gatgactatc    120 tttaatgtat ggaaaatgag agctgcaggt gtaatgaaga ccttctttt gagatctggt    180 aaagatgatt cctgggagag acgcaaacac agccaccacc caagtgatca cacttgtcac    240 cacccccaaag                                                          250

<210> SEQ ID NO 15
<211> LENGTH: 120
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: phosphorothioate-linked DNA
<220> FEATURE:
<221> NAME/KEY: misc_feature
<222> LOCATION: (91)..(120)
<223> OTHER INFORMATION: phosphorothioate-linked DNA

<400> SEQUENCE: 15
tctttaccag atctcaaaaa gaaggtcttc attacacctg cagctctcat tttccataca    60
ttaaagatag tcatcttggg gctggtcctg ccgctgcttg tcatggtcat ctgctactcg    120

<210> SEQ ID NO 16
<211> LENGTH: 120
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: phosphorothioate-linked DNA
<220> FEATURE:
<221> NAME/KEY: misc_feature
<222> LOCATION: (91)..(120)
<223> OTHER INFORMATION: phosphorothioate-linked DNA

<400> SEQUENCE: 16
cgagtagcag atgaccatga caagcagcgg caggaccagc ccaagatga ctatctttaa    60 tgtatggaaa atgagagctg caggtgtaat gaagaccttc tttttgagat ctggtaaaga    120

<210> SEQ ID NO 17
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 77, 78, 79, 80
<223> OTHER INFORMATION: Bridged nucleic acids

<400> SEQUENCE: 17
gaaggtcttc attacacctg cagctctcat tttccataca ttaaagatag tcatcttggg    60
gctggtcctg ccgctgcttg                                                80

<210> SEQ ID NO 18
<211> LENGTH: 80

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10,
      71, 72, 73, 74, 75, 76, 77, 78, 79, 80
<223> OTHER INFORMATION: Bridged nucleic acids

<400> SEQUENCE: 18
gaaggtcttc attacacctg cagctctcat tttccataca ttaaagatag tcatcttggg    60
gctggtcctg ccgctgcttg                                                80

<210> SEQ ID NO 19
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10
<223> OTHER INFORMATION: Bridged nucleic acids

<400> SEQUENCE: 19
gaaggtcttc attacacctg cagctctcat tttccataca ttaaagatag tcatcttggg    60
gctggtcctg ccgctgcttg                                                80

<210> SEQ ID NO 20
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 71, 72, 73, 74, 75, 76, 77, 78, 79, 80
<223> OTHER INFORMATION: Bridged nucleic acids

<400> SEQUENCE: 20
gaaggtcttc attacacctg cagctctcat tttccataca ttaaagatag tcatcttggg    60
gctggtcctg ccgctgcttg                                                80

<210> SEQ ID NO 21
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 4, 5
<223> OTHER INFORMATION: n = 6-Thio-2'-deoxyguanosine
<220> FEATURE:
<221> NAME/KEY: misc_feature
<222> LOCATION: 2, 3, 77, 78, 79, 80
<223> OTHER INFORMATION: Bridged nucleic acids

<400> SEQUENCE: 21
naanntcttc attacacctg cagctctcat tttccataca ttaaagatag tcatcttggg    60
gctggtcctg ccgctgcttg                                                80

<210> SEQ ID NO 22
<211> LENGTH: 80
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 1, 4, 5
<223> OTHER INFORMATION: n = 6-Thio-2'-deoxyguanosine
<220> FEATURE:
<221> NAME/KEY: misc_feature
<222> LOCATION: 2, 3
<223> OTHER INFORMATION: n = 8-Amino-2'-deoxyadenosine
<220> FEATURE:
<221> NAME/KEY: misc_feature
<222> LOCATION: 77, 78, 79, 80
<223> OTHER INFORMATION: Bridged nucleic acids

<400> SEQUENCE: 22
nnnnntcttc attacacctg cagctctcat tttccataca ttaaagatag tcatcttggg    60
gctggtcctg ccgctgcttg                                                80

<210> SEQ ID NO 23
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 4, 5, 73, 76
<223> OTHER INFORMATION: n = 6-Thio-2'-deoxyguanosine
<220> FEATURE:
<221> NAME/KEY: misc_feature
<222> LOCATION: 77, 78, 79, 80
<223> OTHER INFORMATION: Bridged nucleic acids

<400> SEQUENCE: 23
naanntcttc attacacctg cagctctcat tttccataca ttaaagatag tcatcttggg    60
gctggtcctg ccnctncttg                                                80

<210> SEQ ID NO 24
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 4, 5
<223> OTHER INFORMATION: n = 6-Thio-2'-deoxyguanosine
<220> FEATURE:
<221> NAME/KEY: misc_feature
<222> LOCATION: 2, 3
<223> OTHER INFORMATION: n = 8-Amino-2'-deoxyadenosine
<220> FEATURE:
<221> NAME/KEY: misc_feature
<222> LOCATION: 77, 78, 79, 80
<223> OTHER INFORMATION: Bridged nucleic acids

<400> SEQUENCE: 24
nnnnntcttc attacacctg cagctctcat tttccataca ttaaagatag tcatcttggg    60
gctggtcctg ccgctgcttg                                                80

<210> SEQ ID NO 25
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 97, 98, 99, 100
```

<223> OTHER INFORMATION: Bridged nucleic acids

<400> SEQUENCE: 25
gaaggtcttc attacacctg cagctctcat tttccataca ttaaagatag tcatcttggg    60
gctggtcctg ccgctgcttg tcatggtcat ctgctactcg                          100

<210> SEQ ID NO 26
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10,
      91, 92, 93, 94, 95, 96, 97, 98, 99, 100
<223> OTHER INFORMATION: Bridged nucleic acids

<400> SEQUENCE: 26
gaaggtcttc attacacctg cagctctcat tttccataca ttaaagatag tcatcttggg    60
gctggtcctg ccgctgcttg tcatggtcat ctgctactcg                          100

<210> SEQ ID NO 27
<211> LENGTH: 100
<212> TYPE: DNA
<213> ORGANISM: Artificial Sequence
<220> FEATURE:
<221> NAME/KEY: misc_feature
<222> LOCATION: 1, 2, 3, 4, 5, 11, 12, 13, 14, 15,
      86, 87, 88, 89, 90, 96, 97, 98, 99, 100
<223> OTHER INFORMATION: Bridged nucleic acids
<220> FEATURE:
<223> OTHER INFORMATION: Synthetic Construct

<400> SEQUENCE: 27
gaaggtcttc attacacctg cagctctcat tttccataca ttaaagatag tcatcttggg    60
gctggtcctg ccgctgcttg tcatggtcat ctgctactcg                          100

<210> SEQ ID NO 28
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10,
      86, 87, 88, 89, 90, 96, 97, 98, 99, 100
<223> OTHER INFORMATION: Bridged nucleic acids

<400> SEQUENCE: 28
gaaggtcttc attacacctg cagctctcat tttccataca ttaaagatag tcatcttggg    60
gctggtcctg ccgctgcttg tcatggtcat ctgctactcg                          100

<210> SEQ ID NO 29
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 11, 12, 13, 14, 15
<223> OTHER INFORMATION: Bridged nucleic acids

<400> SEQUENCE: 29
gaaggtcttc attacacctg cagctctcat tttccataca ttaaagatag tcatcttggg    60
gctggtcctg ccgctgcttg tcatggtcat ctgctactcg                         100

<210> SEQ ID NO 30
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 86, 87, 88, 89, 90, 96, 97, 98, 99, 100
<223> OTHER INFORMATION: Bridged nucleic acids

<400> SEQUENCE: 30
gaaggtcttc attacacctg cagctctcat tttccataca ttaaagatag tcatcttggg    60
gctggtcctg ccgctgcttg tcatggtcat ctgctactcg                         100

<210> SEQ ID NO 31
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 97, 98, 99, 100
<223> OTHER INFORMATION: Bridged nucleic acids
<220> FEATURE:
<221> NAME/KEY: misc_feature
<222> LOCATION: 5, 85, 86, 93
<223> OTHER INFORMATION: n = 6-Thio-2'-deoxyguanosine
<220> FEATURE:
<221> NAME/KEY: misc_feature
<222> LOCATION: 11, 14, 89, 96
<223> OTHER INFORMATION: n = 8-Amino-2'-deoxyadenosine

<400> SEQUENCE: 31
gaagntcttc nttncacctg cagctctcat tttccataca ttaaagatag tcatcttggg    60
gctggtcctg ccgctgcttg tcatnntcnt ctnctnctcg                         100

<210> SEQ ID NO 32
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 4, 5, 85, 86, 93, 100
<223> OTHER INFORMATION: n = 6-Thio-2'-deoxyguanosine
<220> FEATURE:
<221> NAME/KEY: misc_feature
<222> LOCATION: 2, 3, 11, 14, 89, 96
<223> OTHER INFORMATION: n = 8-Amino-2'-deoxyadenosine
<220> FEATURE:
<221> NAME/KEY: misc_feature
<222> LOCATION: 6, 7, 8, 9, 12, 13, 91, 97, 98, 99
<223> OTHER INFORMATION: Bridged nucleic acids

<400> SEQUENCE: 32
nnnnntcttc nttncacctg cagctctcat tttccataca ttaaagatag tcatcttggg    60
gctggtcctg ccgctgcttg tcatnntcnt ctnctnctcn                         100

<210> SEQ ID NO 33
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 4, 5, 85, 86, 100
<223> OTHER INFORMATION: n = 6-Thio-2'-deoxyguanosine
<220> FEATURE:
<221> NAME/KEY: misc_feature
<222> LOCATION: 2, 3, 89
<223> OTHER INFORMATION: n = 8-Amino-2'-deoxyadenosine
<220> FEATURE:
<221> NAME/KEY: misc_feature
<222> LOCATION: 11, 12, 13, 14, 94, 95, 96
<223> OTHER INFORMATION: Bridged nucleic acids

<400> SEQUENCE: 33
nnnnntcttc attacacctg cagctctcat tttccataca ttaaagatag tcatcttggg    60
gctggtcctg ccgctgcttg tcatnntcnt ctgctactcn                         100

<210> SEQ ID NO 34
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 78, 79, 90, 91, 94, 95, 96
<223> OTHER INFORMATION: Bridged nucleic acids
<220> FEATURE:
<221> NAME/KEY: misc_feature
<222> LOCATION: 76, 80, 85, 86, 100
<223> OTHER INFORMATION: n = 6-Thio-2'-deoxyguanosine
<220> FEATURE:
<221> NAME/KEY: misc_feature
<222> LOCATION: 83, 89
<223> OTHER INFORMATION: n = 8-Amino-2'-deoxyadenosine

<400> SEQUENCE: 34
gaaggtcttc attacacctg cagctctcat tttccataca ttaaagatag tcatcttggg    60
gctggtcctg ccgctncttn tcntnntcnt ctgctactcn                         100

<210> SEQ ID NO 35
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10,
        78, 79, 90, 91, 94, 95, 96
<223> OTHER INFORMATION: Bridged nucleic acids
<220> FEATURE:
<221> NAME/KEY: misc_feature
<222> LOCATION: 76, 80, 85, 86, 100
<223> OTHER INFORMATION: n = 6-Thio-2'-deoxyguanosine
<220> FEATURE:
<221> NAME/KEY: misc_feature
<222> LOCATION: 83, 89
<223> OTHER INFORMATION: n = 8-Amino-2'-deoxyadenosine

<400> SEQUENCE: 35
gaaggtcttc attacacctg cagctctcat tttccataca ttaaagatag tcatcttggg    60
gctggtcctg ccgctncttn tcntnntcnt ctgctactcn                         100

<210> SEQ ID NO 36
<211> LENGTH: 100
<212> TYPE: DNA
<213> ORGANISM: Artificial Sequence -continued

```
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 72, 73, 74, 75,
      76, 77, 78, 79, 80, 91, 92, 93, 94, 95, 96, 97, 98, 99, 100
<223> OTHER INFORMATION: Bridged nucleic acids

<400> SEQUENCE: 36
gaaggtcttc attacacctg cagctctcat tttccataca ttaaagatag tcatcttggg      60
gctggtcctg ccgctgcttg tcatggtcat ctgctactcg                          100

<210> SEQ ID NO 37
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 11, 12, 13, 14, 15, 72, 73, 74, 75, 76,
      86, 87, 88, 89, 90, 96, 97, 98, 99, 100
<223> OTHER INFORMATION: Bridged nucleic acids

<400> SEQUENCE: 37
gaaggtcttc attacacctg cagctctcat tttccataca ttaaagatag tcatcttggg      60
gctggtcctg ccgctgcttg tcatggtcat ctgctactcg                          100

<210> SEQ ID NO 38
<211> LENGTH: 34
<212> TYPE: DNA
<213> ORGANISM: Artificial Sequence
<220> FEATURE:
<223> OTHER INFORMATION: Synthetic Construct

<400> SEQUENCE: 38
gcgaggacta tctttaatgt atggaaaatc tcgc                                 34

<210> SEQ ID NO 39
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 8, 9, 10, 11, 12, 13, 14, 15, 16,
      17, 18, 19, 20, 21, 22, 23, 24, 25, 26, 27
<223> OTHER INFORMATION: Bridged nucleic acids

<400> SEQUENCE: 39
gcgaggacta tctttaatgt atggaaaatc tcgc                                 34

<210> SEQ ID NO 40
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 13, 14, 15, 16,
      17, 18, 19, 20, 21, 22, 23
<223> OTHER INFORMATION: Bridged nucleic acids

<400> SEQUENCE: 40
gcgaggacta tctttaatgt atggaaaatc tcgc                                 34
```

<210> SEQ ID NO 41
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 14, 15, 16, 17, 18, 19, 20, 21
<223> OTHER INFORMATION: Bridged nucleic acids

<400> SEQUENCE: 41
gcgaggacta tctttaatgt atggaaaatc tcgc                              34

<210> SEQ ID NO 42
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15, 16, 17, 18, 19, 20
<223> OTHER INFORMATION: Bridged nucleic acids

<400> SEQUENCE: 42
gcgaggacta tctttaatgt atggaaaatc tcgc                              34

<210> SEQ ID NO 43
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17, 18, 19
<223> OTHER INFORMATION: Bridged nucleic acids

<400> SEQUENCE: 43
gcgaggacta tctttaatgt atggaaaatc tcgc                              34

<210> SEQ ID NO 44
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 16, 17, 18, 19, 23
<223> OTHER INFORMATION: Bridged nucleic acids

<400> SEQUENCE: 44
gcgaggacta tctttaatgt atggaaaatc tcgc                              34

<210> SEQ ID NO 45
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 16, 17, 18, 19
<223> OTHER INFORMATION: Bridged nucleic acids

<400> SEQUENCE: 45
gcgaggacta tctttaatgt atggaaaatc tcgc                              34

<210> SEQ ID NO 46
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 16, 17, 18, 19
<223> OTHER INFORMATION: Bridged nucleic acids

<400> SEQUENCE: 46
gcgaggacta tctttaatgt atggaaaatc tcgc                                34

<210> SEQ ID NO 47
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4, 5, 16, 17, 18, 19
<223> OTHER INFORMATION: Bridged nucleic acids

<400> SEQUENCE: 47
gcgaggacta tctttaatgt atggaaaatc tcgc                                34

<210> SEQ ID NO 48
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: Bridged nucleic acids

<400> SEQUENCE: 48
gcgaggacta tctttaatgt atggaaaatc tcgc                                34

<210> SEQ ID NO 49
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 17, 18, 23
<223> OTHER INFORMATION: Bridged nucleic acids

<400> SEQUENCE: 49
gcgaggacta tctttaatgt atggaaaatc tcgc                                34

<210> SEQ ID NO 50
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 17, 18
<223> OTHER INFORMATION: Bridged nucleic acids

<400> SEQUENCE: 50
gcgaggacta tctttaatgt atggaaaatc tcgc                                    34

<210> SEQ ID NO 51
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 17, 18
<223> OTHER INFORMATION: Bridged nucleic acids

<400> SEQUENCE: 51
gcgaggacta tctttaatgt atggaaaatc tcgc                                    34

<210> SEQ ID NO 52
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4, 5, 17, 18
<223> OTHER INFORMATION: Bridged nucleic acids

<400> SEQUENCE: 52
gcgaggacta tctttaatgt atggaaaatc tcgc                                    34

<210> SEQ ID NO 53
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = 7-Deaza-8-aza-2'-deoxyadenosine
<220> FEATURE:
<221> NAME/KEY: misc_feature
<222> LOCATION: 18
<223> OTHER INFORMATION: n = 5-Propynyl-2'-deoxyuridine
<220> FEATURE:
<221> NAME/KEY: misc_feature
<222> LOCATION: 19
<223> OTHER INFORMATION: n = 2'-Deoxyisoguanosine

<400> SEQUENCE: 53
gcgaggacta tctttnnnnt atggaaaatc tcgc                                    34

<210> SEQ ID NO 54
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = 7-Deaza-8-aza-2'-deoxyadenosine
<220> FEATURE:
<221> NAME/KEY: misc_feature
<222> LOCATION: 18
<223> OTHER INFORMATION: n = 5-Propynyl-2'-deoxyuridine
<220> FEATURE:
<221> NAME/KEY: misc_feature
<222> LOCATION: 19
<223> OTHER INFORMATION: n = 2'-Deoxyisoguanosine
<220> FEATURE:
<221> NAME/KEY: misc_feature

```
<222> LOCATION: 15, 20
<223> OTHER INFORMATION: Bridged nucleic acids

<400> SEQUENCE: 54
gcgaggacta tctttnnnnt atggaaaatc tcgc                                34

<210> SEQ ID NO 55
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = 7-Deaza-8-aza-2'-deoxyadenosine
<220> FEATURE:
<221> NAME/KEY: misc_feature
<222> LOCATION: 18
<223> OTHER INFORMATION: n = 5-Propynyl-2'-deoxyuridine
<220> FEATURE:
<221> NAME/KEY: misc_feature
<222> LOCATION: 19
<223> OTHER INFORMATION: n = 2'-Deoxyisoguanosine
<220> FEATURE:
<221> NAME/KEY: misc_feature
<222> LOCATION: 13, 14, 15, 20, 21, 22
<223> OTHER INFORMATION: Bridged nucleic acids

<400> SEQUENCE: 55
gcgaggacta tctttnnnnt atggaaaatc tcgc                                34

<210> SEQ ID NO 56
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 13, 14, 15, 20, 22
<223> OTHER INFORMATION: n = 5-Propynyl-2'-deoxyuridine
<220> FEATURE:
<221> NAME/KEY: misc_feature
<222> LOCATION: 21
<223> OTHER INFORMATION: n = 7-Deaza-8-aza-2'-deoxyadenosine
<220> FEATURE:
<221> NAME/KEY: misc_feature
<222> LOCATION: 16, 17, 18, 19
<223> OTHER INFORMATION: Bridged nucleic acids

<400> SEQUENCE: 56
gcgaggacta tcnnaatgn nnggaaaatc tcgc                                 34

<210> SEQ ID NO 57
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 13, 14, 15, 20, 22
<223> OTHER INFORMATION: n = 5-Propynyl-2'-deoxyuridine
<220> FEATURE:
<221> NAME/KEY: misc_feature
<222> LOCATION: 16, 17, 18, 19, 21
<223> OTHER INFORMATION: Bridged nucleic acids

<400> SEQUENCE: 57
gcgaggacta tcnnaatgn anggaaaatc tcgc                                 34
```

```
<210> SEQ ID NO 58
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: linked to Lys-Lys-Lys-JTJTTJTTJT-OOO- where
      Lys=lysine, J= pseudoisocytosine, and
      o= flexible 8-amino-3-6-dioxaoctanoic acid
<220> FEATURE:
<221> NAME/KEY: misc_feature
<222> LOCATION: (15)..(15)
<223> OTHER INFORMATION: linked to -Lys-Lys-Lys, where Lys=lysine

<400> SEQUENCE: 58
tcttcttctc atttc                                                    15

<210> SEQ ID NO 59
<211> LENGTH: 31
<212> TYPE: DNA
<213> ORGANISM: Artificial Sequence
<220> FEATURE:
<223> OTHER INFORMATION: Synthetic Construct

<400> SEQUENCE: 59
atcacttggg tggtggctgt gtttgcgtct c                                  31

<210> SEQ ID NO 60
<211> LENGTH: 31
<212> TYPE: DNA
<213> ORGANISM: Artificial Sequence
<220> FEATURE:
<223> OTHER INFORMATION: Synthetic Construct

<400> SEQUENCE: 60
agtagcagat gaccatgaca agcagcggca g                                  31
```

GENOME EDITING USING EFFECTOR OLIGONUCLEOTIDES FOR THERAPEUTIC TREATMENT

CROSS REFERENCE TO RELATED APPLICATIONS

This application is a divisional of U.S. patent application Ser. No. 14/777,490, filed Sep. 15, 2015, which is a National Phase application under 35 U.S.C. § 371 of International Application No. PCT/US2014/026787, filed on Mar. 13, 2014, which claims the benefit of priority of U.S. provisional patent application Ser. No. 61/801,822, filed Mar. 15, 2013 and U.S. provisional patent application Ser. No. 61/867,522, filed Aug. 19, 2013, the contents of which are hereby incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 873892000110SEQLIST.TXT, date recorded: Jul. 21, 2020, size: 27 kB).

BACKGROUND OF THE INVENTION

Oligonucleotides which are partially complementary to genomic DNA sequence can associate with duplex DNA in a sequence specific manner. See, e.g., WO2011/133802. Oligonucleotides comprising sequences that vary in part from corresponding genomic DNA sequences have been used to edit chromosomal DNA by recombination of the sequence encoded by the oligonucleotide into the genome. Whereas oligonucleotides am also used in biological research, a main intended use of oligonucleotides in cell therapy is to correct genetic sequences associated with disease in cells to produce preparations of therapeutic cells for use. However, the efficiency of oligonucleotide-mediated alteration of the genome is very low, limiting the applicability of this approach. At the same time, due to the inefficiency of the process, it is thought that off-target alteration of the genome is also low. Consequently, methods that utilize oligonucleotides to produce therapeutic cells without increasing their low expected off-target activity and that produce increased yields of optimally-modified cells would be of interest to enable more effective and safe cell therapy.

The sequence of an oligonucleotide used to introduce a genetic alteration is typically designed to correspond to one strand of a target double stranded chromosomal DNA sequence of interest, usually the coding sequence or promoter of a gene of interest wherein the oligonucleotide is additionally designed to comprise a mismatch compared to the target sequence. Oligonucleotides are thought to associate with their corresponding target sequences in the genome. In some cases, the mismatched sequence is introduced into the genome following recombination events.

The efficiency of oligonucleotide-mediated alteration of the genome is low. Various publications teach that oligonucleotides should be designed to contain sequences that are essentially identical to their corresponding target sequences in order to work. For example, US 2010/0172882 teaches that a greater number of homologous positions within the oligonucleotide will increase the probability that it will be recombined into the target sequence, target region or target site. Thus, having more mismatches is discouraged by existing publications. Many oligonucleotides used to alter the genome via recombination reported to date have been designed to introduce a point mutation or to change a single base. See, e.g., Bonner M., et al. 1:e18. doi: 10.1038/mtna.2012.9 *Mol. Ther. Nucleic Acids* (2012); Bertoni C, et al. 37(22):7468-82. doi: 10.1093/nar/gkp757 *Nucleic Acids Res.* (2009) and Andrieu-Soler C, et al. *Nucleic Acids Res.* 7; 33(12):3733-42 (2005).

In order to increase the efficiency of genome editing using oligonucleotides, other references (e.g., US 2011/0262406) teach the use of triplex-forming molecules, which is described as a pair of single-stranded molecules, or a single molecule composed of a pair of molecules connected by a linker, that facilitate strand displacement and triplex formation, in which one molecule binding to the target strand by Hoogsteen binding and the other molecule binds to the target strands by Watson-Crick binding in a sequence specific manner. It is thought that these molecules recruit cellular factors that are involved in recombination which work to increase the efficiency with which oligonucleotides designed to edit the genome are recombined into the genome, and they have been used in editing the genome of cells for the treatment of various diseases, such as HIV. The use of multiple compounds here is one way of approaching genomic editing. Nonetheless, even in combination with these molecules, the efficiency of genome modification using oligonucleotides remains low. There is a need to solve the problem of inefficient recombination, inefficient genomic editing, and increased off-target activity, as well as additional benefits of providing for compositions and methods of producing therapeutic cells without increasing their low expected off-target activity and increasing yields of optimally-modified cells.

Human immunodeficiency virus (HIV) has infected millions of people worldwide. Many efforts have been made to combat HIV infection. Some approaches focus on small molecules to affect the virus' replication cycle. Other efforts have focused on the cell therapy side. Since CCR5 is known to be a co-receptor that is needed for many HIV isolates, efforts have been made to target CCR5 for HIV therapy. See, e.g., WO 2009/06336, US 2005/0220772, and US 2009/0202496.

The reported cure of the Berlin Patient has spurred efforts to create cell therapies based on the interpretation that any disruption of CCR5 may underlie a safe and effective cell therapy. One report on a patient study referred to as the "Berlin Patient" described how the patient was cured following a bone marrow transplant using bone marrow derived from a Δ32 homozygous individual, or an individual carrying only this particular variant of the gene and no wild-type or other variant. See, e.g., Allers K, et al. *Blood* 117(10): 2791-9 (2011). The Δ32 variant of CCR5 represents a disrupted variant of the wild-type gene which occurs in a small percentage of North Americans and Europeans but is almost nonexistent in Asians and Africans. In order to infect its target cells, HIV must first dock onto its receptor and co-receptor, CD4 and CCR5, respectively, both of which are expressed on the surface of target cells. Δ32 homozygous individuals are naturally-resistant to HIV/AIDS and otherwise healthy. Thus, it was thought that disruption of CCR5 per se may be used as the basis of an HIV/AIDS cell therapy. However, various mutations of CCR5 (e.g. introduction of stop codon(s)) have not proven to be viable cell therapy approaches.

Attempts have been made to isolate different types of cells, such as stem cells (e.g., cord blood-derived stem cells and hematopoietic stem cells) that have naturally-occurring Δ32 mutations and to expand these isolated stem cells with naturally-occurring Δ32 mutation. However, there has been not much success with expansion of populations of stem cells with naturally occurring Δ32 mutations. There exists many problems with making the appropriate mutations in CCR5 that render the modified cell to be less likely to be infected with HIV. As such, one problem to be solved is the modification of CCR5 in cells that are susceptible to HIV infection such that the resultant cells are less likely to be infected with HIV. In addition, another problem is the isolation and/or expansion of stem cells with the precise Δ32 mutations to the extent that there are enough cells for cell therapy for individual infected with HIV, suspected of having HIV infection or at risk of HIV infection. Furthermore, another problem exists with isolating and/or purifying the right population of stem cells with the precise Δ32 deletion in CCR5.

BRIEF SUMMARY OF THE INVENTION

The invention provides for, inter alia, compositions and methods of making and using effector oligonucleotides that are designed to alter a nucleic acid sequence (target sequence), such as a genomic target sequence. The effector oligonucleotides of the invention can be used for treatment of different conditions and/or diseases where genomic editing of two or more bases can be beneficial. Accordingly, in one aspect, the invention provides for effector oligonucleotides comprising more than one mismatch as compared to its target sequence.

In some aspects, the invention provides for effector oligonucleotides comprising more than one mismatch as compared to its target sequence. In other aspects, the invention provides for effector oligonucleotides comprising 2 to 100 or more mismatches, including effector oligonucleotides comprising mismatches selected from the group consisting of: 2 to 50 mismatches, 2 to 40 mismatches, 2 to 30 mismatches, 5 to 50 mismatches, 5 to 40 mismatches, 5 to 30 mismatches, 10 to 50 mismatches, 10 to 40 mismatches, 10 to 30 mismatches, 15 to 50 mismatches, 15 to 40 mismatches, 15 to 30 mismatches, 20 to 50 mismatches, 25 to 50 mismatches, 25 to 40 mismatches, 2 to 5 mismatches, 6 to 10 mismatches, 11 to 15 mismatches, 16 to 20 mismatches, 21 to 25 mismatches, 26 to 31 mismatches, 32 to 40 mismatches, 30 to 50 mismatches, and 50 or more mismatches as compared to its target sequence.

In any of the embodiments above, the target sequence is any chromosomal or genomic sequence, including a sequence that comprises a gene, or portion thereof, or a sequence that encodes an mRNA or protein, or portion thereof. In some embodiments, the target sequence comprises a known allelic variant or form of the gene or portion thereof, single-nucleotide polymorphism (SNP) form of the gene or portion thereof, a full-length or truncated form of a gene, a mutated form of the gene or a portion thereof, or a combination of any of these. In some embodiments, the target sequence corresponds to a variant of a gene, or portion thereof, that is linked or associated with a disease or infection or susceptibility to a disease or infection.

In any of the embodiments above, the target sequence is a virus receptor. In any of the embodiments above, the mismatch in the effector oligonucleotide relates to a sequence to be deleted from a virus receptor. In any of the embodiments above, the effector oligonucleotide comprises a sequence that does not match a sequence to be deleted, and that comprises matches to the target sequence before the sequence to be deleted and comprises matches to the target sequence after the sequence to be deleted. In any of the embodiments above, the effector oligonucleotide has about 10 to 200 matches to the target sequence before the sequence to be deleted. In any of the embodiments above, the effector oligonucleotide has about 10 to 200 matches to the target sequence after the sequence to be deleted. In any of the embodiments above, the effector oligonucleotide has about 10 to 200 matches to the target sequence before the site deletion and about 10 to 200 matches to the target sequence after the site of deletion. In any of the embodiments above, the effector oligonucleotide has about 40 to 200 matches to the target sequence before the sequence to be deleted. In any of the embodiments above, the effector oligonucleotide has about 40 to 200 matches to the target sequence after the sequence to be deleted. In any of the embodiments above, the effector oligonucleotide has about 40 to 200 matches to the target sequence before the site deletion and about 40 to 200 matches to the target sequence after the site of deletion. In any of the embodiments above, the effector oligonucleotide has about 10 to 40 matches to the target sequence before the sequence to be deleted. In any of the embodiments above, the effector oligonucleotide has about 10 to 40 matches to the target sequence after the sequence to be deleted. In any of the embodiments above, the effector oligonucleotide has about 10 to 40 matches to the target sequence before the sequence to be deleted and about 10 to 40 matches to the target sequence after the sequence to be deleted. In any of the embodiments above, the effector oligonucleotide has about 40 to 200 matches to the target sequence before the sequence to be deleted and about 10 to 40 matches to the target sequence after the sequence to be deleted. In any of the embodiments above, the effector oligonucleotide has about 10 to 40 matches to the target sequence before the sequence to be deleted and about 40 to 200 matches to the target sequence after the sequence to be deleted.

In any of the embodiments above, wherein the effector oligonucleotide comprises a sequence that does not match a sequence to be deleted, and that comprises matches to the target sequence before the sequence to be deleted and comprises matches to the target sequence after the sequence to be deleted, the sequence to be deleted comprises 2 or more bases (i.e. 2 or more mismatches). In some embodiments, the sequence to be deleted is 10 or more bases long. In some embodiments, the sequence to be deleted is 20 or more bases long. In some embodiments, the sequence to be deleted is 40 or more bases. In some embodiments, the sequence to be deleted consists of 2 to 500 bases. In some embodiments, the sequence to be deleted consists of 20 to 40 bases.

In any of the embodiments above, the target sequence is an HIV receptor. In any of the embodiments above, the HIV receptor is CCR5. In any of the embodiments above, the mismatch in the effector oligonucleotide corresponds to a 32 base target sequence that is deleted in a delta-32 (Δ32) variant of CCR5, wherein the Δ32 variant is compared to the wild-type sequence of CCR5. In any of the embodiments above, the effector oligonucleotide comprises a sequence that comprises matches to the target sequence before the sequence to be deleted and comprises matches to the target sequence after the sequence to be deleted. In any of the embodiments above, the effector oligonucleotide comprises at least 40 matches to a target sequence before the site of the Δ32 deletion in CCR5. In any of the embodiments above, the effector oligonucleotide comprises at least 40 matches to a target sequence after the site of the Δ32 deletion in CCR5. In any of the embodiments above, the effector oligonucleotide is selected from the group consisting of: (a) effector oligonucleotides comprising a sequence that corresponds to the Δ32 variant of CCR5, (b) effector oligonucleotides comprising a sequence that corresponds to the Δ32 variant of CCR5 and that corresponds to a coding sequence of the Δ32 variant of CCR5, and (c) effector oligonucleotides that are designed to mimic the Δ32 variant of CCR5.

In other aspects, the invention provides for compositions comprising any one of the effector oligonucleotides in any of the embodiments above.

In other aspects, the invention provides for isolated, recombinant cells comprising a target sequence corresponding to any one of the effector oligonucleotides in any of the embodiments above. In some embodiments, the isolated, recombinant cells comprise a recombined sequence resulting from the contacting of a cell comprising a target sequence with an effector oligonucleotide targeted to the target sequence. In some embodiments, the isolated, recombinant cells comprise a recombined sequence resulting from the contacting of the cell comprising a target sequence with any one of the recombined sequence corresponding to the effector oligonucleotides in any of the embodiments above In other aspects, the invention provides for methods of genomic editing ex vivo, the method comprising contacting a cell with any one of the effector oligonucleotides in any of the embodiments above under conditions sufficient for entry of the effector oligonucleotide into the cell and allowing the effector oligonucleotide to edit chromosomal DNA of the cell.

In some aspects, the invention provides for the use of an effector oligonucleotide to correct, alter or eliminate the sequence associated with a disease or infection or susceptibility to the disease or infection, wherein the effector oligonucleotide is targeted to a variant of a gene or portion thereof, that is linked or associated with a disease or infection or susceptibility to a disease or infection.

In some aspects, the invention provides for a method of treating a disease in a subject comprising administering to the subject in need thereof an effective amount of an effector oligonucleotide. In some embodiments of the method of treating a disease in a subject, the effector oligonucleotide is targeted to a variant of a gene or portion thereof, that is linked or associated with the disease.

In some aspects, the invention provides for a method of treating an infection in a subject comprising administering to the subject in need thereof an effective amount of an effector oligonucleotide. In some embodiments of the method of treating an infection in a subject, the effector oligonucleotide is targeted to a variant of a gene or portion thereof, that is linked or associated with the infection.

In some aspects, the invention provides for a method of preventing a disease or infection in a subject comprising administering to the subject in need thereof an effective amount of an effector oligonucleotide. In some embodiments of the method of preventing a disease or infection in a subject, the effector oligonucleotide is targeted to a variant of a gene or portion thereof, that is linked or associated with susceptibility to the disease or infection.

In some aspects, the invention provides for a method of making recombinant cells comprising contacting cells comprising a target sequence within a gene to be altered with an effector oligonucleotide targeted to the target sequence and comprising more than one mismatches as compared to the target sequence; and allowing the effector oligonucleotide to alter the target sequence in the cells. In some embodiments, the method of making the recombinant cells having a specific gene alteration comprises: (a) delivering the effector oligonucleotide targeted to a target sequence and comprising more than one mismatch as compared to the target sequence into the cells comprising the target sequence within the gene to be altered; and (b) incubating the cells under conditions sufficient for entry of the effector oligonucleotide into the cells and allowing the effector oligonucleotide to alter the target sequence in the cells, to provide the recombinant cells.

In some aspects, the invention provides for a method of making a substantially enriched population of recombinant cells, the method comprising contacting cells comprising a target sequence within a gene to be altered with an effector oligonucleotide targeted to the target sequence and comprising more than one mismatches as compared to the target sequence; allowing the effector oligonucleotide to alter the target sequence in the cells; isolating at least one of the recombinant cells; and growing the at least one recombinant cell under conditions to provide the substantially enriched population of recombinant cells. In some embodiments, the method of making the substantially enriched population of recombinant cells comprises: (a) delivering the effector oligonucleotide targeted to a target sequence and comprising more than one mismatch as compared to the target sequence into the cells comprising the target sequence within the gene to be altered; (b) incubating the cells under conditions sufficient for entry of the effector oligonucleotide into the cells and allowing the effector oligonucleotide to alter the target sequence in the cells, to provide the recombinant cells; (c) isolating at least one of the recombinant cells; and (d) growing the at least one recombinant cell under conditions to provide the substantially enriched population of recombinant cells. In some embodiments, the substantially enriched population of recombinant cells is further purified by separating the recombinant cells from the growth media and suspending the cells in a suitable media for use in cell therapy.

In some aspects, the invention provides for a method of treating a disease in a subject comprising administering to the subject in need thereof an effective amount of a recombinant cell comprising a recombined sequence resulting from the contacting of a cell comprising a target sequence within a gene with an effector oligonucleotide targeted to the target sequence and comprising more than one mismatch as compared to the target sequence under conditions sufficient for entry of the effector oligonucleotide into the cell and allowing the effector oligonucleotide to alter the target sequence. In some embodiments of the method of treating a disease in a subject, the effector oligonucleotide is targeted to a variant of a gene or portion thereof, that is linked or associated with the disease.

In some aspects, the invention provides for a method of treating an infection in a subject comprising administering to the subject in need thereof an effective amount of a recombinant cell comprising a recombined sequence resulting from the contacting of a cell comprising a target sequence within a gene with an effector oligonucleotide targeted to the target sequence and comprising more than one mismatch as compared to the target sequence under conditions sufficient for entry of the effector oligonucleotide into the cell and allowing the effector oligonucleotide to alter the target sequence. In some embodiments of the method of treating an infection in a subject, the effector oligonucleotide is targeted to a variant of a gene or portion thereof, that is linked or associated with the infection. In some embodiments, the infection is HIV and the subject has or is suspected of having an HIV infection.

In some aspects, the invention provides for a method of preventing a disease or infection in a subject comprising administering to the subject in need thereof an effective amount of a recombinant cell comprising a recombined sequence resulting from the contacting of a cell comprising a target sequence within a gene with an effector oligonucleotide targeted to the target sequence and comprising more than one mismatch as compared to the target sequence under conditions sufficient for entry of the effector oligonucleotide into the cell and allowing the effector oligonucleotide to alter the target sequence. In some embodiments of the method of preventing a disease or infection in a subject, the effector oligonucleotide is targeted to a variant of a gene or portion thereof, that is linked or associated with susceptibility to the disease or infection. In some embodiments, the infection is HIV and the subject is susceptible to infection by HIV.

In any of the embodiments above, the cell is selected from the group consisting of mammalian cells, human cells, animal cells, plant cells, yeast cells, insect cells, and reptilian cells. In any of the embodiments above, the mammalian cell is selected from the group consisting of embryonic stem cells, induced pluripotent stem cells, adult stem cells, hematopoietic stem cells, cord blood stem cells, cancer stem cells, multipotent progenitor cells, lineage-restricted progenitor cells, common myeloid progenitor cells, Granulocyte-macrophage progenitor cells, megakaryocyte-erythroid progenitor cells, immune cells, differentiated immune cells and CD4-positive immune cells. In any of the embodiments above, the method further comprises contacting the cell with triplex-forming oligonucleotides or pseudocomplementary oligonucleotides. In any of the embodiments above, the triplex-forming oligonucleotide comprises a PNA. In any of the embodiments above, the method further comprises detection of the cells comprising the sequence encoded by the effector oligonucleotide by using fluorogenic oligonucleotide probes. In any of the embodiments above, the detected cells are isolated by fluorescence-activated cell sorting.

In some aspects, the invention provides for a composition comprising a recombinant cell comprising an altered target sequence and an effector oligonucleotide targeted to the target sequence. In some embodiments, the effector oligonucleotide is complementary to at least a portion of the altered target sequence without any mismatches. In some embodiments, the altered target sequence is the result of a Δ32 deletion of the CCR5 gene. In some embodiments, the composition further comprises a detection tool. In some embodiments, the detection tool is a fluorogenic oligonucleotide probe as used in Chromovert® technology.

In some aspects, the invention provides for, inter alia, compositions of stem cells and populations of stem cells that have been engineered for modifications in the CCR5 gene and methods of making and using these populations of modified stem cells. These modifications (e.g., Δ32 deletion) result in frameshift mutations that render resultant stem cells and populations of stem cells more refractory to HIV infection.

In one aspect, the invention provides for compositions comprising a substantially pure population of recombinant stem cells, wherein the stem cells comprise a modification in the CCR5 gene that results in a frameshift. In one embodiment the modification is a Δ32 deletion in a CCR5 gene. In other embodiments, the Δ32 mutation comprises deletion of SEQ ID NO:4 from the wild-type CCR5 gene. In any of the embodiments and combination of embodiments herein, at least 5, 10, 15, 20, 25, 30, 35, 40, 45, 50, 60, 70, 80 or 90% of the stem cells in the population comprise the Δ32 deletion. In any of the embodiments and combination of embodiments herein, at least 50% of the stem cells in the population comprise the Δ32 deletion. In any of the embodiments and combination of embodiments herein, 5 to 90%, 10 to 90%, 15 to 90%, 20 to 90%, 25 to 90%, 30 to 90%, 35 to 90%, 40 to 90%, 45 to 90%, or 50 to 90%, of the stem cells in the population comprise the Δ32 deletion. In any of the embodiments and combination of embodiments herein, the stem cell is selected from the group consisting of: embryonic stem cells, induced-pluripotent stem cells, hematopoietic stem cells, adult stem cells, cord blood stem cells, cancer stem cells, multipotent progenitor cells, lineage-restricted progenitor cells, common myeloid progenitor cells, Granulocyte-macrophage progenitor cells and megakaryocyte-erythroid progenitor cells. In any of the embodiments and combination of embodiments herein, the stem cells in the population express one or more of the markers selected from the group consisting of: CD34, CD133, CD105, CD45, CD59, Thy1/CD90, C-kit (CD117) and SLAM family of cell surface markers. In any of the embodiments and combination of embodiments herein, at least 5, 10, 15, 20, 25, 30, 35, 40, 45, 50, 60, 70, 80 or 90% of the stem cells express one or more of the markers selected from the group consisting of: CD34, CD133, CD105, CD45, CD59, Thy1/CD90, C-kit (CD117) and SLAM family of cell surface markers. In any of the embodiments and combination of embodiments herein, at least 50% of the stem cells express one or more of the markers selected from the group consisting of: CD34, CD133, CD105, CD45, CD59, Thy1/CD90, C-kit (CD117) and SLAM family of cell surface markers. In any of the embodiments and combination of embodiments herein, 5 to 90%, 10 to 90%, 15 to 90%, 20 to 90%, 25 to 90%, 30 to 90%, 35 to 90%, 40 to 90%, 45 to 90%, or 50 to 90%, of the stem cells express one or more of the markers selected from the group consisting of: CD34, CD133, CD105, CD45, CD59, Thy1/CD90, C-kit (CD117) and SLAM family of cell surface markers. In any of the embodiments and combination of embodiments herein, the SLAM family of cell surface markers is selected from the group consisting of CD48, CD150, and CD244. In any of the embodiments and combination of embodiments herein, the stem cells in the population do not express one or more of the markers selected from the group consisting of: CD13, CD33, CD71, CD19, and CD61. In any of the embodiments and combination of embodiments herein, the stem cells in the population comprise an RNA corresponding to an intracellular, non-cell-surface-localized or a cell-surface localized stem cell marker. In any of the embodiments and combination of embodiments herein, the stem cell marker is selected from the group consisting of: transcription factor gene families, signal pathway genes, and kinase genes. In any of the embodiments and combination of embodiments herein, the Δ32 deletion is in one allele. In any of the embodiments and combination of embodiments herein, the Δ32 deletion is in both alleles. In any of the embodiments and combination of embodiments herein, the stem cells of the population further comprise a detection tool wherein the detection tool allows for detection of a stem cell with Δ32 deletion. In any of the embodiments and combination of embodiments herein, the detection tool comprises a fluorophore. In any of the embodiments and combination of embodiments herein, the detection tool further comprises a quencher. In any of the embodiments and combination of embodiments herein, the detection tool is a fluorogenic oligonucleotide probe as used in Chromovert® technology.

In other aspects, the invention provides methods of making a composition comprising a substantially pure population of recombinant stem cells, or a population of cells enriched for recombinant stem cells, wherein the stem cells comprise Δ32 deletion in a CCR5 gene, said method comprising: (a) delivering one or more effector oligonucleotides capable of deleting the 32 base pair sequence of SEQ ID NO:4 into one or more stem cell(s); (b) culturing the stem cells to increase the number of stem cells, thereby producing a substantially pure population of recombinant stem cells comprising Δ32 deletion. In any of the embodiments and combination of embodiments herein, the method further comprises introducing a detection tool into the stem cells of step (a). In any of the embodiments and combination of embodiments herein, the detection tool is a fluorogenic oligonucleotide probe as used in Chromovert® technology.

In other aspects, the invention provides methods of treating an individual with HIV infection or at risk of HIV infection comprising administering to the individual an effective amount of any of the compositions of modified stem cells and/or composition comprising a population of modified stem cells disclosed herein. In any of the embodiments and combination of embodiments herein, the compositions of modified stem cells and/or composition comprising a population of modified stem cells are autologous to the individual.

In other aspects, the invention provides for methods of treating an individual in need thereof comprising administering a pharmaceutically acceptable composition comprising one or more effector oligonucleotides in any of the embodiments above.

In other aspects, the invention provides for methods of treating an individual in need thereof comprising administering a pharmaceutically acceptable composition comprising the recombinant cells of in any of the embodiments above. In any of the embodiments above, the individual has or is suspected of having human immunodeficiency virus (HIV) infection.

In any of the embodiments above, the effector oligonucleotide is a non-naturally occurring oligonucleotide.

BRIEF DESCRIPTION OF THE DRAWINGS

FIG. 1 shows the coding sequence of the CCR5 gene (SEQ ID NO:1) with the 32 bases that are deleted in the Δ32 variant of CCR5 underlined.

FIG. 2 provides the corresponding protein sequences of wild-type CCR5 (SEQ ID NO:2), also indicating the sequence maintained in the Δ32 variants of CCR5. The amino acids of the wild-type variant of CCR5 that are preserved in the Δ32 variant are indicated in non-underlined text. As the 32 base deletion of the Δ32 variant of CCR5 introduces a frame-shift mutation, the Δ32 variant lacks the amino acids of the wild-type variant of CCR5 indicated in underlined text.

FIG. 3 depicts the Δ32 CCR5 protein sequence (SEQ ID NO:3) with the novel 31 amino acid C-terminal tail resulting from the Δ32 deletion underlined.

FIG. 4A depicts effector oligonucleotides used to introduce genomic alterations of greater that one base. Chemical modifications used, if any, are listed. All of these oligos correspond to the sequence of the Δ32 variant of the CCR5 gene. All oligos were synthesized by Genelink, Inc. and gel purified. Note that the letters 'T' or "B" in the oligo name refers to whether the sequence of the oligo corresponds to the sense or antisense strand, respectively. Each oligo name contains two numbers separated by a period. The first number indicates the number of bases in the oligo that match the sequence of the CCR5 gene prior to the site of the 32 base deletion and the second number indicates the number of bases in the oligo that match the sequence of the CCR5 gene following the site of the 32 base deletion present in the Δ32 variant of the CCR5 gene.

FIG. 4B depicts the position of each effector oligonucleotide relative to the sequence of the Δ32 variant of CCR5. The two long horizontal lines indicate a portion of the CCR5 sequence. The thick vertical line indicates the site of the 32 base deletion that characterizes the Δ32 versus the wild-type variant of the CCR5 gene. The distance between every two vertical lines indicates 10 bases. The position of each effector oligonucleotide relative to this sequence is indicated by a horizontal line for each effector oligonucleotide, which is identified using its numerical identifier. Effector oligonucleotides 1, 3, 5, 7 and 19 correspond in sequence to the sense or coding strand, whereas effector oligonucleotides 2, 4, 6, 8 and 20 correspond in sequence to the non-coding strand.

DETAILED DESCRIPTION OF THE INVENTION

Figure 4B:
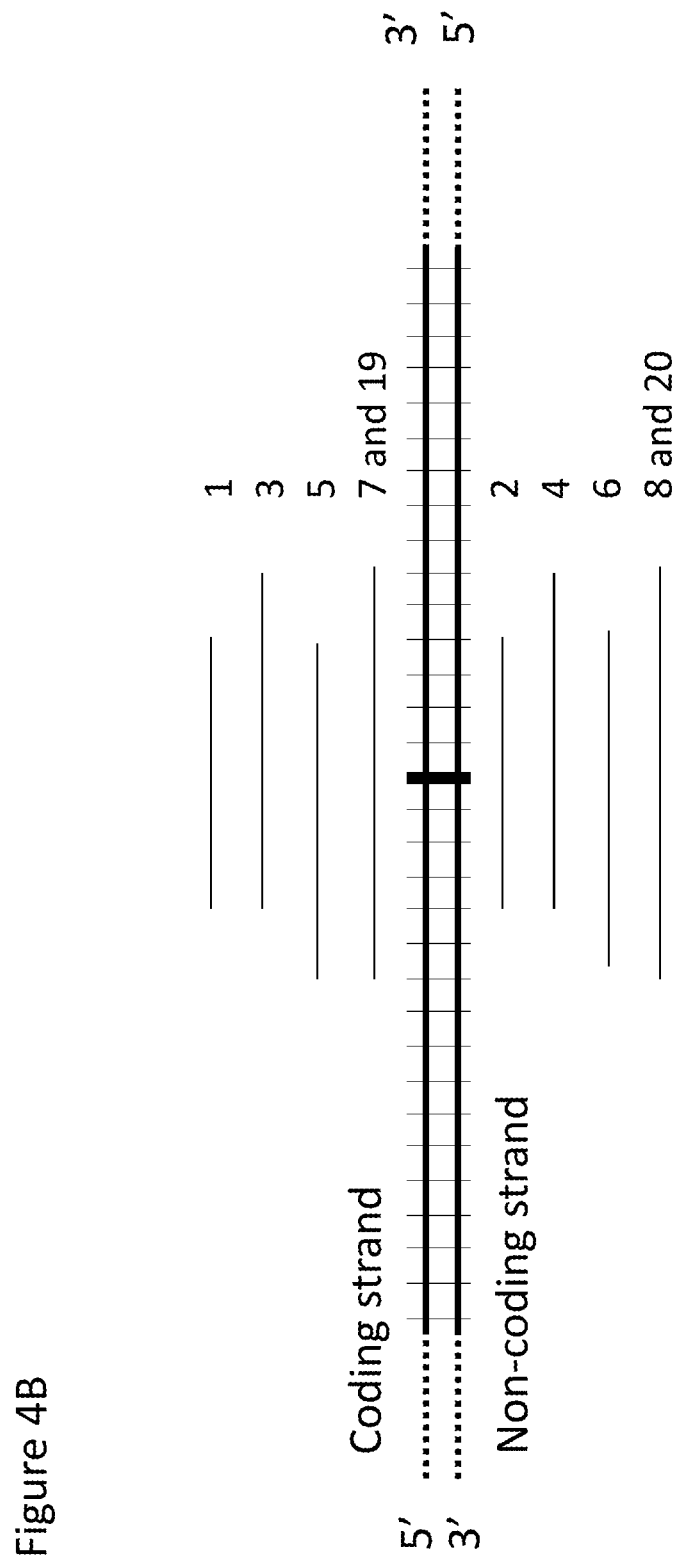
FIG. 4B shows the alignment of the effector oligonucleotides against their corresponding genomic target.

The invention provides compositions and methods of making and using effector oligonucleotides, including effector oligonucleotides with greater than one mismatch as compared to its target sequence. These effector oligonucleotides are useful for improving the efficiency of genomic editing as well as providing therapeutic benefits to individuals in need thereof. The invention also provides compositions of recombinant cells and populations of recombinant cells that have been engineered for modifications in gene sequences using the effector oligonucleotides as described herein.

The invention also provides for, inter alia, compositions of recombinant cells and populations of recombinant cells that have been engineered for modifications in a gene. In some embodiments, the recombinant cells are stem cells engineered for modifications in the CCR5 gene. In some embodiments, these modifications (e.g., Δ32 deletion) result in a frameshift mutation that render the stem cells and cells differentiated from these stem cells (and any intermediate cells in between) less likely to become infected by HIV. These recombinant stem cells are useful for treating individuals with HIV infection, suspected of having HIV infection, and/or at risk of HIV infection. The invention also provides for methods for making and using these recombinant stem cells for cell therapy. The recombinant stem cells can differentiate, transdifferentiate or de-differentiate during the course of the treatment but the common trait is that the stem cells contain the modifications to CCR5 (e.g, Δ32 mutation) described herein such that the stem cells (and any intermediate and resultant cell population) are more refractory to HIV infection.

A. General Techniques

The practice of the present invention will employ, unless otherwise indicated, conventional techniques of stem cell biology, cell culturing, molecular biology (including recombinant techniques), microbiology, cell biology, biochemistry and immunology, which are within the skill of the art. Such techniques are explained fully in the literature, such as, *Molecular Cloning: A Laboratory Manual*, third edition (Sambrook et al., 2001) Cold Spring Harbor Press; *Oligonucleotide Synthesis* (Herdewijn, ed., 2004); *Animal Cell Culture* (R. I. Freshney, ed., 1987); *Methods in Enzymology* (Academic Press, Inc.; *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993); *Short Protocols in Molecular Biology* (Wiley and Sons, 1999), *Embryonic Stem Cells: A Practical Approach* (Notaranni et al. eds., Oxford University Press 2006); *Essentials of Stem Cell Biology* (R. Lanza, ed., Elsevier Academic Press 2006); *Stem Cell Assays (Methods in Molecular Biology)* (Mohan C. Vemuri, Ed., Humana Press; first edition (Aug. 10, 2007); *Mesenchymal Stem Cells: Methods and Protocols (Methods in Molecular Biology)* (Darwin J. Prockop, Donald G. Phinney, Bruce A. Bunnell, Eds., first edition (Mar. 7, 2008)); *Handbook of Stem Cells* (Robert Lanza, et al., Eds., Academic Press (Sep. 14, 2004); Stem Cell Culture Vol 86: *Methods in Cell Biology* (Jennie P. Mather, Ed., Academic Press, first edition (May 15, 2008)); *Practical Hematopoietic Stem Cell Transplantation* (Andrew J. Cant, et al. Eds., Wiley-Blackwell, first edition (Jan. 22, 2007)); *Hematopoietic Stem Cell Protocols* (Kevin D. Bunting, Ed., Humana Press, 2nd ed. edition (Jan. 31, 2008)); *Bone Marrow and Stem Cell Transplantation (Methods in Molecular Medicine)* (Meral Beksac, Ed., Humana Press; first edition (May 3, 2007)); *Stem Cell Therapy and Tissue Engineering for Cardiovascular Repair: From Basic Research to Clinical Applications* (Nabil Dib, et al., Eds., Springer, first edition (Nov. 16, 2005)); *Blood And Marrow Stem Cell Transplantation: Principles, Practice, And Nursing Insights* (Kim Schmit-Pokorny (Author) and Susan Ezzone (Editor), Jones & Bartlett Publishers; third edition (May 22, 2006)); *Hematopoietic Stem Cell Protocols* (Christopher A. Klug and Craig T. Jordan, Eds., Humana Press; first edition (Dec. 15, 2001)); and *Clinical Bone Marrow and Blood Stem Cell Transplantation* (Kerry Atkinson, et al., Eds., Cambridge University Press; third edition (Dec. 8, 2003)).

B. Definitions

As used herein, the singular form "a", "an", and "the" includes plural references unless indicated otherwise. For example, "an" effector oligonucleotide includes one or more Effector oligonucleotides.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects of the invention described herein include "comprising," "consisting," and "consisting essentially of" aspects.

As used interchangeably herein, the terms "polynucleotides" or "oligonucleotide" or "oligo" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside. Oligonucleotides can also include non-naturally occurring bases (e.g. modified or substituted bases). Oligonucleotides may additionally comprise one or more covalently attached or linked compounds, toxins, proteins, enzymes, hormones, signaling molecules, fluorescent molecules, quenchers, chemicals and linkers or a combination thereof. Oligonucleotides may comprise one or more portions or bases that are covalently crosslinked or attached to other portions or bases.

A "non-naturally occurring oligonucleotide" as used herein refers to an oligonucleotide having at least one modification or substitution in the internucleoside linkage, sugar moiety or the nucleoside base not found in natural nucleic acids. The effector oligonucleotides as described herein include non-naturally occurring oligonucleotides, as further described herein.

A "target sequence" as used herein generally refers to any nucleic acid sequence, such as a genomic sequences, that is to be altered by the effector oligonucleotide, e.g. by contacting a cell with the effector oligonucleotide under conditions suitable to alter the genomic sequence in the cell. The target sequence can be a sequence within a gene of interest, i.e. a gene to be altered, such that the gene of interest can be altered by altering the target sequence. The effector oligonucleotide matches, or is complementary to, at least a portion of the target sequence, and also includes at least a portion that does not match the target sequence, or wherein the target sequence includes a portion that does not match the effector oligonucleotide (e.g. having at least 2 or more mismatches).

A "mismatch" or "mismatches" as used herein refers to portions of an effector oligonucleotide that do not match portions of a target sequence, or portions of the target sequence that do not match the effector oligonucleotide, as described herein. The mismatches can be insertions (e.g. additional bases in the effector oligonucleotide not matching the target sequence, resulting in addition of bases to the target sequence), deletions (e.g. bases missing from the effector oligonucleotide that are in the target sequence, e.g. wherein the effector oligonucleotide has portions matching a portion of the target sequence prior to and a portion of the sequence after a sequence that is in the target sequence that does not match the effector oligonucleotide, resulting in deletion of the unmatched sequence from the target sequence), or non-complementary bases (e.g. resulting in alterations in the target sequence), or any combinations thereof. The effector oligonucleotide is designed to result in altering the target sequence, for example where the resulting altered target sequence matches the effector oligonucleotide without any mismatches.

An "individual," "subject" or "patient" is a vertebrate. In certain embodiments, the vertebrate is a mammal. Mammals include, but are not limited to, primates (including human and non-human primates), pets (e.g., dogs, cats, rabbits, etc.), agricultural animals (e.g., cows, livestock, etc.), sport animals (e.g., horses), and rodents (e.g., mice and rats). In certain embodiments, a mammal is a human.

An "effective amount" or a "sufficient amount" of a substance is that amount sufficient to effect beneficial or desired results, including clinical results, and, as such, an "effective amount" depends upon the context in which it is being applied. In the context of administering a composition that comprises one or more effector oligonucleotides of the invention, an effective amount of an effector oligonucleotide is an amount sufficient to achieve recombination of the effector oligonucleotide at its corresponding target site in the genome as compared to recombination of the effector oligonucleotide at other sites in the genome, or to achieve a greater rate or frequency of recombination of the effector oligonucleotide at its corresponding target site in the genome as compared to the rate or frequency of recombination of the effector oligonucleotide at other sites in the genome in cells treated with the effector oligonucleotide. When used in the treatment or prophylaxis context, or in the context of palliating pain or alleviating the symptoms of a particular condition, an effective amount, e.g. of an effector oligonucleotide, or of a recombinant cell resulting from alteration mediated by an effector oligonucleotide, is an amount sufficient to effect beneficial or desired results, including clinical results. An effective amount can be administered in one or more administrations. For purposes of this invention, for example, an effective amount of recombinant cells (e.g. Δ32 CCR5 stem cells) is a certain amount of the modified cells that can reduce one of more symptoms of the conditions for which the individual is being treated (e.g., HIV viral burden). As an example, an effective amount of modified stem cells (e.g. Δ32 CCR5 stem cells) encompasses the use of these modified stem cells when they are being grown or proliferated in their pluripotent, undifferentiated state as well as the use of modified stem cells when they have been cultured further to induce them to differentiate down a particular pathway. When used in the context of "assisting therapy," an effective amount enhances a therapeutic regimen (as compared to a regimen lacking the modified stem cells) and, as such, provides a beneficial or desired result.

As used herein, and as well-understood in the art, "treatment" or "treating" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment. "Treatment" or "treating" can also mean conferring resistance to infection. "Receiving treatment" includes initial treatment and/or continuing treatment. In some aspects, treatment with a one or more cells disclosed herein is accompanied by no or fewer side effects than are associated with currently available therapies. In the context of this invention, the symptoms of AIDS and any AIDS-related conditions are encompassed within this scope.

"Palliating" a disease or disorder means that the extent and/or undesirable clinical manifestations of a disorder or a disease state are lessened and/or time course of the progression is slowed or lengthened, as compared to not treating the disorder. Especially in the case of HIV/AIDS, as is well understood by those skilled in the art, this can include one or more of the following: reducing viral load, or the concentration or count of virus, in the individual or in the bodily fluids of the individual, increasing the number of CD4-positive immune cells in the individual, increasing the strength of immune system, the efficiency or reliability of the immune system or the immune response in individuals, decreasing or inhibiting the replication or propagation of HIV in the individual, decreasing or eliminating the integration of the genetic material corresponding to HIV into the genome of the cells of the individual, decreasing or rendering inhospitable or uninfectable the potential cellular targets or reservoirs in the individual that may be infected by HIV or used by HIV to replicate or propagate, eliminating from the individual the cells in the individual that are infected or infectable by HIV or in which the genetic material of HIV has become integrated, mitigating or decreasing the side-effects or negative effects of HIV/AIDS on the tissues or organs of the individual, and/or decreasing the infectiousness of the individual or the propensity or ability of the individual to infect others via infected bodily fluids. Further, palliation does not necessarily occur by administration of one dose, but often occurs upon administration of a series of doses of a treatment or therapy. Thus, an amount of a treatment or therapy sufficient to palliate a response or disorder may be administered in one or more administrations.

As used herein, "refractory" or "resistant" to HIV infection refers to the reduction of (or lessening of) HIV infection in cells that are susceptible to HIV infection. It can be a lessening of the rate of infection, lessening the viral burden of cells infected, reducing the viral burden in a biological sample being tested as well as at the cellular level. It is not intended to require that 100% of the cells in a particular population or sample are not infected.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, the method may reduce the probability of disease development in a given time frame and/or reduce the extent of the disease in a given time frame, when compared to not using the method. In some aspects, such comparisons are based on clinical studies using a statistically significant number of individuals. Disease development can be detectable using standard clinical techniques. Development may also refer to disease progression that can be initially undetectable and includes occurrence, recurrence, and onset.

As used herein, "in need thereof" includes individuals who have a condition or disease or are "at risk" for the condition or disease. As used herein, an "at risk" individual is an individual who is at risk of development of a condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, diet, history of previous disease, presence of precursor disease, genetic (i.e., hereditary) considerations, breeding protocols and considerations, and environmental exposure.

"Stem cells" as used herein refers to cells with self-regeneration capacities and the ability to become another type of cell in its differentiation pathway. As used herein, stem cells are cells that are totipotent, pluripotent, multipotent, oligopotent and/or unipotent.

As used herein, "delta-32" and "Δ32" are interchangeable and refers to a stretch of 32 bases in the CCR5 sequence that is removed from the sequence of CCR5 (see FIG. 1).

As used herein, the term "isolated population" of stem cells refers to a population of one or more stem cells that have been manipulated to provide a preparation of cells that is substantially free of additional components (e.g., cellular debris). Various aspects of isolated populations are described herein. The term "isolated population" of stem cells can also refer to a population of one or more stem cells that have been manipulated or enriched for cells that have been manipulated, including genetically manipulated, that have been isolated or enriched from a population of cells that were treated to manipulate them. For example, some population of cells that are treated to form the altered cells will not be altered, and the altered cell population can be isolated or enriched relative to the unaltered population.

As used herein, the term "homogeneous population" and "highly homogeneous population" and "enriched population" of stem cells refer to a population of cells where a significant portion of the population is stem cells, or where a population of stem cells is altered to provide a recombinant stem cell which can be enriched relative to the unaltered stem cells, or where a significant portion of the population is stem cells having a specific genotype with respect to one or more sequences or markers. Various embodiments reflecting homogeneity including degrees of homogeneity are described herein and can also be described using the term "substantially pure" or "substantially enriched".

"Purity" as used to describe the purity of stem cells does not necessarily refer to the presence of only stem cells in the composition but rather indicates that the stem cells have been manipulated such that they have been removed from their natural tissue environment and indicates their relationship to the other cells present in the resulting population. "Purity" as used to describe the purity of stem cells can also indicate that the stem cells have been manipulated such that they have a specific genotype with respect to one or more sequences or markers.

By "pharmaceutically acceptable carrier" is meant any material which, when combined with an active ingredient, allows the ingredient to retain biological activity and does not provoke an unacceptable immune response (e.g., a severe allergy or anaphylactic shock) based on the knowledge of a skilled practitioner. Examples include, but are not limited to, any of the standard pharmaceutical carriers such as carboxymethylcellulose (CMC), phosphate buffered saline solutions, water, emulsions such as oil/water emulsion, and various types of wetting agents. Exemplary diluents for aerosol or parenteral administration are phosphate buffered saline or normal (0.9%) saline. An exemplary carrier for the infusion of cells is CMC. Compositions comprising such carriers are formulated by well known conventional methods (see, for example, *Remington's Pharmaceutical Sciences*, 18th edition, A. Gennaro, ed., Mack Publishing Co., Easton, Pa., 1990; and *Remington, The Science and Practice of Pharmacy* 20th Ed. Mack Publishing, 2000, which are each hereby incorporated by reference in their entireties, particularly with respect to formulations).

General reference to "the composition" or "compositions" includes and is applicable to compositions of the invention. The invention also provides pharmaceutical compositions comprising the components described herein.

C. Effector Oligonucleotides

Effector oligonucleotides are oligonucleotides of varying length that can bind to target sequences. Different types of target sequences, including those genes with causal or correlative relationship to diseases and disease states are contemplated within the scope of the invention. Different types of target sequences, including those genes with causal or correlative relationship to infections or susceptibility to infection by infectious agents or viruses are contemplated within the scope of the invention. Target sequences are described in greater detail below.

In one aspect, the effector oligonucleotide has one mismatch as compared to its target sequence. In other aspects, the effector oligonucleotide has more than one mismatch as compared to its target sequence. These effector oligonucleotides with mismatch(es) can be used to produce greater alterations of the genome, for instance to add, substitute or delete more than one DNA base from a target sequence. Such genomic alterations of the genome could be used for instance to add, alter or delete amino acids to an encoded protein, modify a promoter sequence and its activity, modify a splice site and alternative splicing, modify other gene-regulatory elements or DNA binding sites within the genome. Accordingly, effector oligonucleotides of the invention can have more than one mismatch, such as 2 to 500 mismatches, for example, greater than 2, 3, 4, 5, 6, 7, 8, 9, 10, 11 to 15, 16 to 25, 26 to 40, 41 to 100 or great than 100 mismatches. In some embodiments, the effector oligonucleotide has 2 to 500, 2 to 400, 2 to 300, 2 to 200, 2 to 100, 5 to 500, 5 to 400, 5 to 300, 5 to 200, 5 to 100, 10 to 500, 10 to 400, 10 to 300, 10 to 200, 10 to 100, 15 to 500, 15 to 400, 15 to 300, 15 to 200, 15 to 100, 20 to 500, 20 to 400, 20 to 300, 20 to 200, 20 to 100, 25 to 500, 25 to 400, 25 to 300, 25 to 200, 25 to 100, 30 to 500, 30 to 400, 30 to 300, 30 to 200, 30 to 100, 35 to 500, 35 to 400, 35 to 300, 35 to 200, 35 to 100, 40 to 500, 40 to 400, 40 to 300, 40 to 200, 40 to 100, 45 to 500, 45 to 400, 45 to 300, 45 to 200, 45 to 100, 50 to 500, 50 to 400, 50 to 300, 50 to 200, 50 to 100, 2 to 75, 2 to 50, 2 to 40, 2 to 30, 5 to 75, 5 to 50, 5 to 40, 5 to 30, 10 to 75, 10 to 50, 10 to 40, 10 to 30, 15 to 75, 15 to 50, 15 to 40, 15 to 30, 20 to 75, 20 to 50, 20 to 40, 20 to 30, 25 to 75, 25 to 50, 25 to 40, 25 to 30, 30 to 75, 30 to 50, 30 to 40, 2 to 5, 6 to 10, 11 to 15, 16 to 20, 21 to 25, 26 to 31, 32 to 40, 40 to 50, or 50 or more mismatches as compared to its target sequence.

Effector oligonucleotides that can be used to alter the genome by more than one DNA base are described. These effector oligonucleotides can be synthesized to have varying lengths, including 20 to 10000 bases, for instance 20, 20-500, 20-400, 20-300, 20-200, 20-100, 21-30, 31-40, 41-50, 51-60, 61-70, 71-80, 81-90, 91-100, 100-500, 100-400, 100-300, 100-200, 101-120, 121-140, 141-160, 161-180, 181-200, 200-500, 200-400, 200-300, 201-250, 251-300, 300-500, 300-400, 301-350, 351-400, 401-500, 500-600, 600-700, 700-800, 800-900, 900-1000, 1000-1500, 1500-2000, 2000-3000, 3000-4000, 4000-5000, 5000-10000, or greater than 10000 bases. The effector oligonucleotides may comprise one or more sites that comprise a mismatch to their corresponding target sequences, where at least one of these sites comprises a mismatch that is 2-100 mismatched bases, such as at least of 2, 3, 4, 5, 6, 7, 8, 9, 10, 11, 12, 13, 14, 15, 16, 17, 18, 19, 20, 20-25, 25-30, 31, 32, 33, 34, 35, 35-40, 40-50, 50-60, 60-70, 70-80, 80-90, 90-100, or greater than 100 mismatched bases. Where two or more sites within an effector oligonucleotide comprise mismatched bases, the two or more sites may each be spaced apart from another by 1-100 bases, such as 1, 2, 3, 4, 5, 6, 7, 8, 9, 10, 11, 12, 13, 14, 15, 16, 17, 18, 19, 20, 20-25, 25-30, 31, 32, 33, 34, 35, 35-40, 40-50, 50-60, 60-70, 70-80, 80-90, 90-100 or greater than 100 bases.

Effector oligonucleotides can be used to alter the genome by deletion of a sequence from a gene. In some embodiments, such effector oligonucleotides comprise a sequence that matches a first portion of a target sequence and a second portion of a target sequence, wherein the first portion of the target sequence is before the sequence to be deleted and the second portion of the target sequence is after the sequence to be deleted, wherein the effector oligonucleotide does not match the sequence to be deleted. In some embodiments, the effector oligonucleotide comprises the sequence that matches the first portion of the target sequence directly linked to a sequence that matches the second portion of the target sequence. In some embodiments, the sequence that matches the target sequence before the sequence to be deleted is 10 to 500, 10 to 400, 10 to 300, 10 to 200, 10 to 125, 10 to 60, 20 to 500, 20 to 400, 20 to 300, 20 to 200, 20 to 125, 20 to 60, 30 to 500, 30 to 400, 30 to 300, 30 to 200, 30 to 125, 30 to 60, 40 to 500, 40 to 400, 40 to 300, 40 to 200, 40 to 125, or 40 to 60 bases. In some embodiments, the sequence that matches the target sequence after the sequence to be deleted is 10 to 500, 10 to 400, 10 to 300, 10 to 200, 10 to 125, 10 to 60, 20 to 500, 20 to 400, 20 to 300, 20 to 200, 20 to 125, 20 to 60, 30 to 500, 30 to 400, 30 to 300, 30 to 200, 30 to 125, 30 to 60, 40 to 500, 40 to 400, 40 to 300, 40 to 200, 40 to 125, or 40 to 60 bases. In some embodiments, the sequence that matches the target sequence before the sequence to be deleted is 10 to 500, 10 to 400, 10 to 300, 10 to 200, 10 to 125, 10 to 60, 20 to 500, 20 to 400, 20 to 300, 20 to 200, 20 to 125, 20 to 60, 30 to 500, 30 to 400, 30 to 300, 30 to 200, 30 to 125, 30 to 60, 40 to 500, 40 to 400, 40 to 300, 40 to 200, 40 to 125, or 40 to 60 bases and the sequence that matches the target sequence after the sequence to be deleted is 10 to 500, 10 to 400, 10 to 300, 10 to 200, 10 to 125, 10 to 60, 20 to 500, 20 to 400, 20 to 300, 20 to 200, 20 to 125, 20 to 60, 30 to 500, 30 to 400, 30 to 300, 30 to 200, 30 to 125, 30 to 60, 40 to 500, 40 to 400, 40 to 300, 40 to 200, 40 to 125, or 40 to 60 bases. In some embodiments, the sequence to be deleted from the gene is 2 to 500, 2 to 400, 2 to 300, 2 to 200, 2 to 100, 5 to 500, 5 to 400, 5 to 300, 5 to 200, 5 to 100, 10 to 500, 10 to 400, 10 to 300, 10 to 200, 10 to 100, 15 to 500, 15 to 400, 15 to 300, 15 to 200, 15 to 100, 20 to 500, 20 to 400, 20 to 300, 20 to 200, 20 to 100, 25 to 500, 25 to 400, 25 to 300, 25 to 200, 25 to 100, 30 to 500, 30 to 400, 30 to 300, 30 to 200, 30 to 100, 35 to 500, 35 to 400, 35 to 300, 35 to 200, 35 to 100, 40 to 500, 40 to 400, 40 to 300, 40 to 200, 40 to 100, 45 to 500, 45 to 400, 45 to 300, 45 to 200, 45 to 100, 50 to 500, 50 to 400, 50 to 300, 50 to 200, 50 to 100, 2 to 75, 2 to 50, 2 to 40, 2 to 30, 5 to 75, 5 to 50, 5 to 40, 5 to 30, 10 to 75, 10 to 50, 10 to 40, 10 to 30, 15 to 75, 15 to 50, 15 to 40, 15 to 30, 20 to 75, 20 to 50, 20 to 40, 20 to 30, 25 to 75, 25 to 50, 25 to 40, 25 to 30, 30 to 75, 30 to 50, 30 to 40, 2 to 5, 6 to 10, 11 to 15, 16 to 20, 21 to 25, 26 to 31, 32 to 40, 40 to 50, or 50 or more bases. In some embodiments, the sequence to be deleted is 1-100 bases (i.e. 1-100 bases not matched to the effector oligonucleotide), 1-200 bases, 1-300 bases, 1-400 bases, or 1-500 bases, such as 1, 2, 3, 4, 5, 6, 7, 8, 9, 10, 11, 12, 13, 14, 15, 16, 17, 18, 19, 20, 1-90, 1-80, 1-70, 1-60, 1-50, 20-25, 25-30, 31, 32, 33, 34, 35, 35-40, 40-50, 50-60, 60-70, 70-80, 80-90, 90-100, or greater than 100 bases representing a sequence to be deleted from the gene.

Effector oligonucleotides can be produced using DNA bases or chemically modified DNA bases. Chemical modifications can include modifications of DNA bases, sugars, and linkages between these, or any combination of these, to provide a non-naturally occurring effector oligonucleotide. Effector oligonucleotides can comprise one or more different kinds of chemical modifications. In some embodiments, phosphorothioate linkages can be used. Numerous modifications are known in the art and may all be considered for use. In particular, modifications used in siRNAs or antisense oligonucleotides would be of interest, as well as chemical modifications that increase the strength of oligonucleotide binding or hybridization to target sequences, specificity of oligonucleotide hybridization to target sequences, efficiency and/or consistency of oligonucleotide delivery into cells, and/or resistance, stability or half-life of the oligonucleotides to degradation in buffers and in cells. Non-limiting examples of chemical modifications that may be used include: one or more of the sugar-phosphodiester type backbone, 2'OH, base can be modified. The substitution of the phosphodiester linkage includes but is not limited to —OP(OH)(O)O—, —OP(O$^-$M$^+$)(O)O—, —OP(SH)(O)O—, —OP(S$^-$M$^+$)(O)O—, —NHP(O)$_2$O—, —OC(O)$_2$O—, —OCH$_2$C(O)$_2$NH—, —OCHC(O)$_2$O—, —OP(CH$_3$)(O)O—, —OP(CH$_2$C$_6$H$_5$)(O)O—, —P(S)(O)O— and —OC(O)$_2$NH—. M$^+$ is an inorganic or organic cation. The backbone can also be peptide nucleic acid (PNA), where the deoxyribose phosphate backbone is replaced by a pseudo peptide backbone. Peptide nucleic acid is described by Hyrup and Nielsen, *Bioorganic & Medicinal Chemistry* 4:5-23, 1996, and Hydig-Hielsen and Godskesen, WO 95/32305, each of which is hereby incorporated by reference herein.

The 2' position of the sugar includes but is not limited to H, OH, $C_1$-$C_4$ alkoxy, OCH$_2$—CH=CH$_2$, OCH$_2$—CH=CH—CH$_3$, OCH$_2$—CH=CH—(CH$_2$).CH$_3$ (n=0, 1 . . . 30), halogen (F, Cl, Br, I), $C_1$-$C_6$ alkyl and OCH$_3$. $C_1$-$C_4$ alkoxy and $C_1$-$C_6$ alkyl may be or may include groups which are straight-chain, branched, or cyclic.

The oligonucleotide may also include one or more bridged nucleotides (BNA), i.e. nucleic acids having at least one sugar having a bridge between two of the sugar ring positions, such as 1', 4' or 2', 4' or 3', 4' bridged sugar moieties. See, for example, Takeshi Imanishi and Satoshi Obika, *Chem. Commun.*, 2002, 1653-1659; Mitsuoka et al., *Nucleic Acids Research*, 2009, 37(4):1225-1238; Hari et al., *Tetrahedron*, 2003, 59:5123-5128; Rahman et al., *Angew. Chem. Int. Ed.*, 2007, 46:4306-4309; Rahman et al., *J. Am. Chem. Soc.*, 2008, 130:4886-4896.

The bases of the nucleotide can be any one of adenine, guanine, cytosine, thymine, uracil, inosine, or the forgoing with modifications. Modified bases include but are not limited to N4-methyl deoxyguanosine, deaza or aza purines and pyrimidines. Ring nitrogens such as the N1 of adenine, N7 of guanine, N3 of cytosine can be alkylated. The pyrimidine bases can be substituted at position 5 or 6, and the purine bases can be substituted at position 2, 6 or 8. See, for example, Cook, WO 93/13121; Sanger, *Principles of Nucleic Acid Structure*, Springer-Verlag, New York (1984), incorporated herein by reference.

Derivatives of the conventional nucleotide are well known in the art and include, for example, molecules having a different type of sugar. The 04' position of the sugar can be substituted with S or $CH_2$. For example, a nucleotide base recognition sequence can have cyclobutyl moieties connected by linking moieties, where the cyclobutyl moieties have hetereocyclic bases attached thereto. See, e.g., Cook et al., International Publication WO 94/19023 (hereby incorporated by reference herein).

Other chemical modifications of oligonucleotides (e.g. probes, effector oligonucleotides) useful in facilitating the delivery of the oligonucleotides into cells include, but are not limited to, cholesterol, transduction peptides (e.g., TAT, penetratin, etc.).

One or more of the sugar-phosphodiester type backbone, 2'OH and purine or pyrimidine base is modified. In one embodiment, the deoxyribose backbone is replaced by peptide nucleic acid.

Effector oligonucleotides can be designed such that at least one of the one or more sites of the mismatched bases in the effector oligonucleotide relative to their corresponding genomic target is at any position within the oligo, including at its 5' end, 3' end, or at a point within the oligo, for instance positioned at a site that is located at a site from the 5' end of the oligo that corresponds to 5%, 5-10%, 10-20%, 20-30%, 30-40%, 40-50%, 50-60%, 60-70%, 70-80%, 80-90%, or 90-95% of the total length of the oligo.

The mismatched bases in the effector oligonucleotides may introduce into the genome an alteration of the DNA sequence that adds, substitutes or deletes bases from the corresponding genomic target of the effector oligonucleotide following recombination of the effector oligonucleotide into the genome. Addition of bases can be used to 1) introduce frame shift mutations, 2) encode additional amino acids at the N-terminus, C-terminus or within the protein encoded by the target genetic sequence where this sequence is a protein-coding sequence, 3) modify the promoter of a gene of interest for instance to increase or decrease or to conditionally increase or decrease its activity, 4) modify a gene-regulatory or DNA-binding sequence element, 5) introduce silent mutations or optimize codons in the coding sequence of a gene of interest, 6) modify splicing recognition sites within the genome. Alteration of bases can be used to 1) alter amino acids at the N-terminus, C-terminus or within the protein encoded by the target genetic sequence where this sequence is a protein-coding sequence, 2) modify the promoter of a gene of interest for instance to increase or decrease or to conditionally increase or decrease its activity, 3) modify a gene-regulatory or DNA-binding sequence element, 5) introduce silent mutations or optimize codons in the coding sequence of a gene of interest, 6) modify splicing recognition sites within the genome. Deletion of bases can be used to 1) introduce frame shift mutations, 2) delete amino acids at the N-terminus, C-terminus or within the protein encoded by the target genetic sequence where this sequence is a protein-coding sequence, 3) modify the promoter of a gene of interest for instance to increase or decrease or to conditionally increase or decrease its activity, 4) modify a gene-regulatory or DNA-binding sequence element, 5) introduce silent mutations or optimize codons in the coding sequence of a gene of interest, or 6) modify splicing recognition sites within the genome.

Exemplary effector oligonucleotides include, without limitation, an effector oligonucleotide engineered to generate the Δ32 variant of CCR5, wherein the effector oligonucleotide has a sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, and SEQ ID NO:37. In some embodiments, the effector oligonucleotide has a sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16. In some embodiments, the effector oligonucleotide has a sequence selected from the group consisting of SEQ ID NO:5, SEQ ID NO:6, SEQ ID NO:7, SEQ ID NO:8, SEQ ID NO:9. SEQ ID NO:10, SEQ ID NO:11, SEQ ID NO:12, SEQ ID NO:15, and SEQ ID NO:16. SEQ ID NOs:5-16 are provided in FIG. 4A, and SEQ ID NOs:17-37 are provided in Example 3.

Compositions comprising effector oligonucleotides are contemplated within the scope of the invention. In some aspects, the composition includes a pharmaceutically acceptable excipient. By "pharmaceutically acceptable," it is meant the carrier, diluent or excipient must be compatible with the other ingredients of the formulation and not deleterious to the recipient thereof. Pharmaceutically acceptable excipients are well known in the art and include sterile water, isotonic solutions such as saline and phosphate buffered saline, and other excipients known in the art. See, e.g., *Remington: The Science and Practice of Pharmacy* (19th edition, 1995. Gennavo, ed.).

D. Target Sequences and Regions

Effector oligonucleotides interact with target sequences and/or target regions. The intended effect is on the target sequence(s) and/or target regions. In some embodiments, the target sequence is chromosomal DNA. In other embodiments, the target sequence is genomic DNA.

The target sequence can be any chromosomal or genomic sequence, including a sequence that comprises a gene or a sequence that encodes an mRNA or protein. Target sequences can comprise any gene, including any known allelic variant or form of the gene, single-nucleotide polymorphism (SNP) form of the gene, the full-length or truncated form of the gene, a mutated form of the gene, or a combination of any of these. Target sequences can also correspond to a variant of a gene that is linked or associated with a disease or infection or susceptibility to a disease or infection, wherein corresponding effector oligonucleotides can be used to correct, alter or eliminate the sequence associated with the disease or infection or susceptibility to the disease or infection. Target sequences can also comprise DNA sequence that comprises in part host genomic sequence and that in addition also comprises in part genomic sequence derived from a foreign source or agent, including following an integration event, for instance the viral sequence introduced into the genome following integration of virally-encoded nucleic acid sequence. Variants or forms of a gene that are associated or linked with a disease or infection or susceptibility to a disease or infection can include the wild-type or predominant form of the gene, or they can vary from the wild-type variant or form of the gene by one or more bases, wherein the variable one or mom bases have a different sequence, are additional bases or are bases that are missing or that have been deleted compared to the wild-type or predominant form of the gene.

Target sequences that encode an RNA or protein can encode any RNA or protein, including an alternatively spliced form of the RNA or protein, or a known genetic variant of the RNA or protein, including a known genetic variant of the RNA or protein associated with or linked with a disease or infection or susceptibility to a disease or infection.

The target sequence can also be a chromosomal or genomic DNA sequence that comprises a regulatory element, including a regulatory element that can regulate or influence the expression level of a gene, for instance a promoter or the binding site of a transcription factor. The target sequence can be a DNA regulatory element that can influence DNA folding or structure, including genome organization or accessibility. Additional examples of target sequences include sequences that comprise exons, introns, consensus sequences for exon-intron recognition sites, sequences that bind proteins, repetitive DNA elements, sequences that comprise telomeres or telomeric repeats, sequences that correspond to centromeres, or sequences that encode RNAs including coding or non-coding RNAs, structural RNAs, mRNAs, inhibitory RNAs, antisense RNAs, RNAs that mediate RNA interference and/or RNAs with catalytic activity. Depending on the nature or type of a target sequence to be edited, the target sequence can comprise any number of bases ranging from 5 to 50000, 5 to 10, 10 to 30, 30 to 40, 40 to 100, 100 to 200, 200 to 500, 500 to 1000, 1000 to 2000, 2000 to 5000, 5000 to 10,000, 10,000 to 15000, 15000 to 20000, 20000 to 50000 or greater than 50000 bases.

In the case of a target sequence that comprises a variant form or sequence of a gene that is correlated, associated or linked to a disease or infection or to susceptibility to a disease or infection, effector oligonucleotides corresponding to the target sequence can be designed to correct the variant or to alter it such that its correlation, association or linkage to the disease or infection or susceptibility to the disease of infection is altered, reduced, or eliminated.

In the case of a target sequence that comprises a variant form or sequence of a gene that is correlated, associated or linked to a physiological or biological function that is implicated in health or disease, effector oligonucleotides corresponding to the target sequence can be designed to alter the variant such that its associated or linked physiological or biological function is altered, enhanced, reduced, activated or eliminated.

In the case of a target sequence that comprises a promoter or gene-regulatory element, effector oligonucleotides corresponding to the target sequence may be designed for use and used to alter the sequence to increase, decrease, alter, enhance, or eliminate the function or activity of the target sequence.

Effector oligonucleotides may be used to alter any target sequence in the genome by changing the sequence, or adding to or deleting from the sequence. This alteration can comprise 1-100, 1-200, 1-300, 1-400, 1-500, or more bases, such as 1, 2, 3, 4, 5, 6, 7, 8, 9, 10, 11-15, 15-20, 20-25, 26-30, 31, 32, 33-40, 41-50, 50-60, 60-70, 70-100, or more than 100 bases. In some embodiments, the alteration comprises consecutive bases, e.g. addition or deletion of a sequence. In some embodiments, the alteration comprises non-consecutive bases, or more than one set of consecutive bases, for example deletion of one or more bases from different (non-consecutive) locations in the target sequence, or addition and/or deletion of more than one sequence, where the two added and/or deleted sequences are not consecutive, or any combinations thereof.

Target sequences can be in genes or gene regions that are associated with, correlate with or cause diseases, or susceptibility to disease or infection, and other physiological conditions. The effector oligonucleotides of the invention can be used to target sequences where two or more bases produce disease or result in susceptibility to a disease. In some instances, the target sequence is a virus receptor, such as an HIV receptor. One non-limiting example is Acquired Immune Deficiency Syndrome (AIDS) that is caused by human immunodeficiency virus (HIV). The effector oligonucleotide target sequence is an HIV receptor, such as CCR5. In one example, the mismatch in the effector oligonucleotide is a deletion. For example, the effector oligonucleotide does not match a target sequence to be deleted, but matches the sequences in the target that are before and after the sequence to be deleted. In one example, a 32 base target sequence is deleted in a Δ32 variant of CCR5, wherein the Δ32 variant is compared to the wild-type sequence of CCR5. The effector oligonucleotide comprises a sequence that comprises matches to the target sequence before the Δ32 sequence to be deleted and comprises matches to the target sequence after the Δ32 sequence to be deleted, but does not match the Δ32 sequence to be deleted. Such deletions can be similarly effected in any target sequence to provide the resulting cell having the desired sequence deleted.

E. Methods of Using Effector Oligonucleotides for Genomic Editing

Effector oligonucleotides can be contacted with cells or introduced into cells. Various parameters can be altered to increase the efficiency of effector oligonucleotide-mediated alteration of the genome. Parameters, and any combinations thereof, that can be adjusted to increase the efficiency of the process include any of: alteration of the conditions used to introduce effector oligonucleotides into cells, including use of cells at particular points in the cell cycle, stimulation of the cells used, varying methods used to introduce effector oligonucleotides into cells, including electroporation or chemically-mediated oligonucleotide introduction, varying the density of cells exposed to effector oligonucleotides, varying the concentration of effector oligonucleotides, varying incubation times and temperatures used during introduction of the effector oligonucleotides and following this step, as well as adding varying concentrations of one or more reagents thought to increase nucleic acid introduction into cells, or the recombination frequencies or efficiency of effector oligonucleotide recombination with the genome of cells, during the steps used to introduce effector oligonucleotides into cells as well as during prior and subsequent incubation steps. PNA reagents or pseudocomplementary oligonucleotides (such as those taught in U.S. Pat. No. 8,309,356, the disclosure of which is hereby incorporated herein by reference) and other molecules that target and bind to or in the vicinity of the sequences targeted by effector oligonucleotides may also be used to increase the efficiency of effector oligonucleotide-mediated alteration of the genome.

Cells enriched or selected for cells at particular points in the cell cycle can be used to increase the efficiency of effector oligonucleotide-mediated alteration of the genome. The organization of the genome of a cell and the accessibility of particular genes in a cell may vary depending on the conditions used to culture cells or the stage or point of the cells in the cell cycle (including mitosis, G0, G1, G2 or S-phase or senescence). The cells used may be cultured under different culture conditions or they may be synchronized in order to enrich or select for cells at a particular stage or point in the cell cycle. For instance nutrient-rich or nutrient-depleted media may be used to culture cells (for instance the concentration of serum, growth factors, cytokines, sugars, amino acids, vitamins, growth hormones or any one or more of these or other reagents used in tissue culture may be varied). Additionally, conditioned media may be used or the cells may be cultured in the presence of feeder or irradiated cells. The cells used may be synchronized at any stage or point of the cell cycle using chemical agents, by nutrient-deprivation, or by mechanical harvesting methods. Mechanical harvesting methods to synchronize cells include taking advantage of the lower adherence of mitotic cells to the surface of growth chamber vessels whereby tapping the vessels causes their preferential release into culture, which can then be collected to enrich for mitotic cells. The cells may be used while they are arrested in a stage of the cell cycle or following release from such arrest. One or more of these methods may be applied to any type of cell, providing cells under different conditions or states.

The stimulation of the cells used can also be adjusted to increase the efficiency of effector oligonucleotide-mediated alteration of the genome. The cells used may be stimulated or treated with chemicals or reagents at any point during the steps of the method, including prior, during or following introduction of effector oligonucleotides into cells, for instance using electroporation. For example, the cells may be exposed to growth factors, cell signaling factors, hormones, cytokines, nutrients, toxins, mutagens, drugs, sugars, ingredients of tissue culture media, serum, proteins, chemicals, small molecules or a mixture of one or more of these. Such agents may alter the growth properties or state of the cells, the permeability of the cells, the organization of the genome of the cells, the accessibility of target genes within the cells, the expression of genes including target genes by the cells, the viability of the cells or other properties of the cells.

Methods used to introduce effector oligonucleotides into cells, including electroporation or chemically-mediated effector oligonucleotide introduction can also be adjusted to increase the efficiency of effector oligonucleotide-mediated alteration of the genome. Depending on cell type, a great number of methods exist that can be used to introduce molecules such as oligonucleotides, chemically modified oligonucleotides and labeled oligonucleotides into cells. Nucleic acids including effector oligonucleotides may be introduced into the cells using known means. Techniques for introducing nucleic acids into cells are well-known and readily appreciated by the skilled worker. The methods include but are not limited to transfection, viral delivery, protein or peptide mediated insertion, coprecipitation methods, lipid based delivery reagents (lipofection), cytofection, lipopolyamine delivery, dendrimer delivery reagents, electroporation or mechanical delivery. Examples of transfection reagents are GENEPORTER, GENEPORTER2, LIPOFECTAMINE, LIPOFECTAMINE 2000, FUGENE 6, FUGENE HD, TFX-10, TFX-20, TFX-50, OLIGOFECTAMINE, TRANSFAST, TRANSFECTAM, GENESHUTTLE, TROJENE, GENESILENCER, X-TREMEGENE, PERFECTIN, CYTOFECTIN, SIPORT, UNIFECTOR, SIFECTOR, TRANSIT-LT1, TRANSIT-LT2, TRANSIT-EXPRESS, IFECT, RNAI SHUTILE, METAFECTENE, LYOVEC, LIPOTAXI, GENEERASER, GENEJUICE, CYTOPURE, JETSI, JETPEI, MEGAFECTIN, POLYFECT, TRANSMESSANGER, RNAiFECT, SUPERFECT, EFFECTENE, TF-PEI-KIT, CLONFECTIN, and METAFECTINE. In addition to the use of chemical reagents used to transfect these and other molecules into cells, electroporation may be used. Also, mechanical means may be used, including for instance passing a mixture of cells in the presence of the molecules to be introduced through a syringe needle several times or by cell scraping, where a cell scraper is used to scrape cells growing in a culture vessel in the presence of the molecule to be introduced. Additionally, pore-forming reagents may be used to create holes in cell membranes through which the molecules to be introduced may pass. Other methods include nanoparticles that are designed to pierce cells, where these may be complexed with or coated by the molecule to be delivered. Ballistic methods including gene-guns may also be used. Passive diffusion of molecules added to culture media may also be used. The method of choice depends on the cell type to be used and extensive teaching in the art exists such that the appropriate method for a given cell type or application may be selected.

Another parameter than can be adjusted to increase the efficiency of effector oligonucleotide-mediated alteration of the genome is varying the density of cells exposed to effector oligonucleotides. Cell densities ranging from 10,000 cells/ml or fewer to 10,000,000 cells/ml or greater may be used. In some embodiments, the cell density ranges from 10,000 cells/ml to 100,000,000 cells/ml, 10,000 cells/ml to 50,000,000 cells/ml, 10,000 cells/ml to 10,000,000 cells/ml, 50,000 cells/ml to 10,000,000 cells/ml, 100,000 cells/ml to 10,000,000 cells/ml, 500,000 cells/ml to 10,000,000 cells/ml or 1,000,000 cells/ml to 10,000,000 cells/ml when exposed to the effector oligonucleotide, The concentration of cells used may depend on the method that is used to introduce reagents such as effector oligonucleotides or fluorogenic probes into cells.

Another parameter than can be adjusted to increase the efficiency of effector oligonucleotide-mediated alteration of the genome is the concentration of effector oligonucleotides. The concentration of effector oligonucleotides to be used can range from nM to mM concentrations, for example ranging from 1 nM to 1000 mM, 50 nM to 100 mM, or 100 nM to 1 mM. In most cases, effector oligonucleotides would be used at μM concentrations, for example 0.1 μM to 1000 μM, 0.1 to 100 μM, 0.1 to 50 μM, 0.1 to 10 μM, or 0.1 to 1 μM. The exact concentration of the effector oligonucleotide used can be optimized empirically depending on factors including the cell type and method of delivery used, as well as for instance the accessibility of the target or the efficiency with which a particular effector oligonucleotide is recombined into the genome at its corresponding target site.

Efficiency of effector oligonucleotide-mediated alteration of the genome can also be increased by varying incubation times used during introduction of the effector oligonucleotide into cells. In methods used to expose or contact cells to effector oligonucleotides or to introduce effector oligonucleotides into cells, there are a number of possible incubation steps the length or duration of any of which can be varied, including but not limited to: 1) depending on the delivery method used, reagents used to mediate or facilitate oligonucleotide delivery may be incubated or pre-incubated with the effector oligonucleotide, 2) the cells may be incubated with effector oligonucleotide, possibly in the presence of other reagents, and 3) the cells may be incubated with the effector oligonucleotide following steps such as electroporation, chemically-mediated or mechanical methods used to introduce the effector oligonucleotides. These incubations may be from 1 to 5 minutes to 1 to 5 hours to overnight or longer. For instance, following the step used to introduce effector oligonucleotides into cells, the cells may be incubated or cultured without removal of the effector oligonucleotides or the media used during this step. In this case, the cells may be incubated for multiple days in the same medium used during this step, or additional media may be added at some later point following at least 1 to 2 hours to 1 to 5 days or more time in culture.

Efficiency of effector oligonucleotide-mediated alteration of the genome can also be increased by varying temperatures used during one or more of the incubation steps. In some embodiments, for the incubations described herein, the temperature may vary from ice cold (i.e., 0 to 4° C.) to 65° C., depending on the length of incubation. Generally, incubation temperatures that are compatible with cell viability range from ice cold to 37° C. or 37-45° C. Higher incubations may also be used, for instance up to or greater than 45° C. to 70° C., however, depending on the cell type, these incubations must be from 1 to 5 minutes to less than 60 minutes in order to preserve cell viability. In most cases, incubations will range in temperature from ice cold to 37° C.

Another parameter than can be adjusted to increase the efficiency of effector oligonucleotide-mediated alteration of the genome is by adding varying concentrations of one or more reagents thought to increase nucleic acid introduction into cells or to increase recombination frequencies or efficiencies in cells. Reagents that may be used include DMSO or other solvents that are thought to play a role in cell permeability and oligonucleotide/DNA/genome structure/accessibility or the association between two or more nucleic acids, including effector oligonucleotides and target sequences. In the case of DMSO, concentrations ranging from 0.1% to 5% would be most preferred, although for shorter incubations concentrations up to 10% or higher may be used. Other reagents to be used here include polyethylene glycol, heparin and/or dextrans of varying lengths.

The number of effector oligonucleotide used may be varied to increase the efficiency of effector oligonucleotide-mediated alteration of the genome. In one embodiment, two or more effector oligonucleotides to different genes may be used. Alternatively, two or more effector oligonucleotides to the same gene but directed to different portions of the same gene may be used, where detection of cells positive for recombination mediated by each of these different effector oligonucleotides may be used to enrich for cells having had undergone recombination at both chromosomal loci of the target gene. Additionally, two or more effector oligonucleotides designed to alter the same point or sequence on the same gene or target may be used, where for instance each of the effector oligonucleotides may be varied in length or by chemical modification. In this case, the effector oligonucleotides would all be designed to correspond to one strand of the target sequence, such that they do not hybridize to each other.

I. Cells for Use with Effector Oligonucleotides

Figure 5:
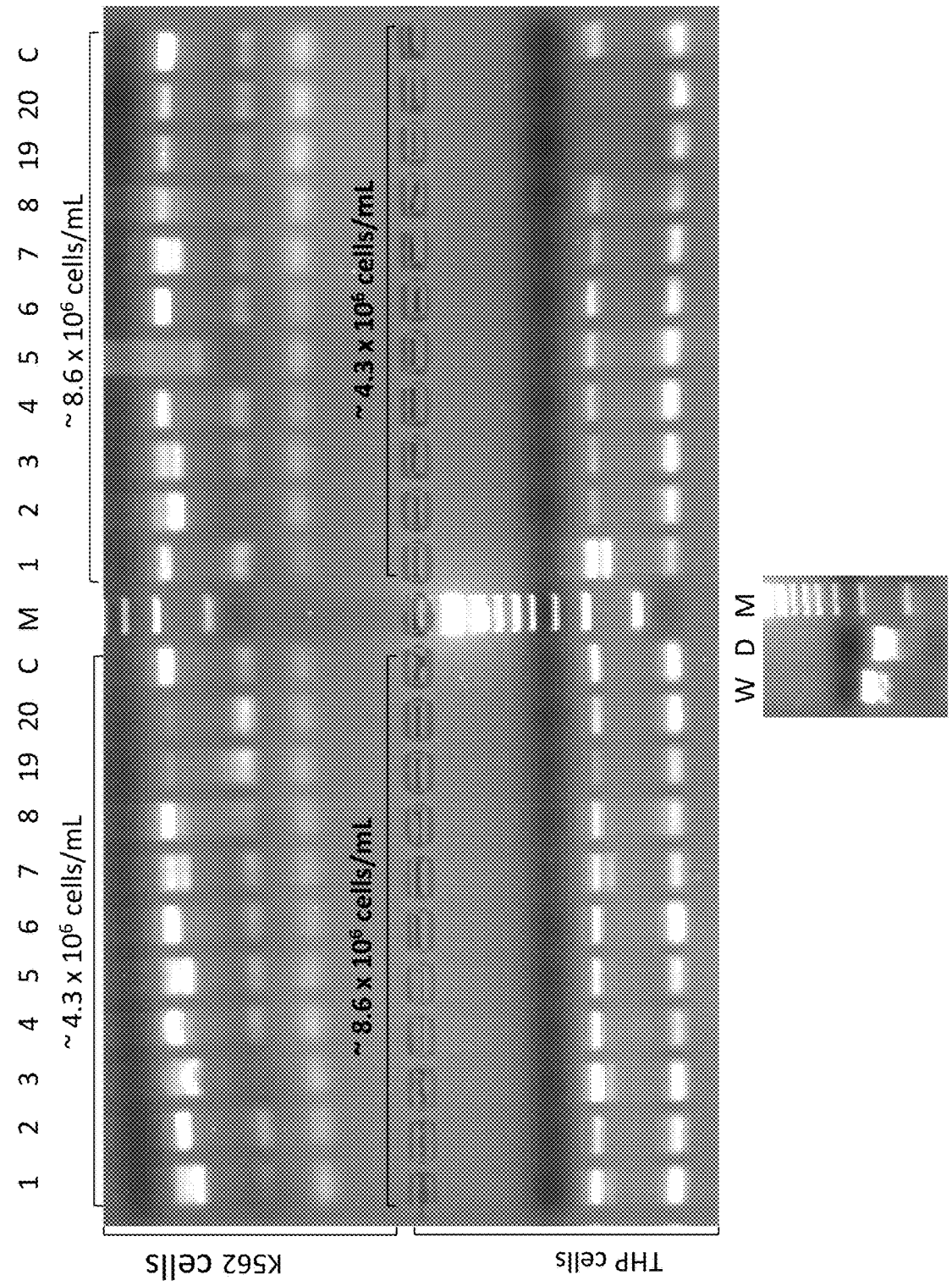
FIG. 5 depicts the genomic PCR results showing detection of effector oligonucleotide-mediated alteration of the genome using effector oligonucleotides to introduce genomic alterations of greater than one base. K562 cells and THP cells were electroporated with the effector oligonucleotides as indicated above each lane by the numbering provided in FIG. 1A i.e. as 1, 2, 3, 4, 5, 6, 7, 8, 19, 20 or "C" (control without effector oligonucleotide). K562 and THP cells were each electroporated at a high (1,000,000 cells/~120 μl) or low (500,000 cells/~120 μl) cell density. The top row shows results for K562 cells at low (columns 1-12) and high (columns 14-23) cell densities. The bottom row shows results for THP cells electroporated at high (columns 1-12) and at low (columns 14-23) cell densities. "M" indicates columns loaded with molecular weight marker (column 13, top and bottom rows). The genomic PCR was performed on genomic DNA obtained from the cells approximately 2 days following electroporation using CCR5-specific genomic primers. The small gel at the bottom of the figure shows PCR results using plasmid containing wild-type CCR5 (lane marked W) or plasmid comprising the Δ32 CCR5 mutation (lane marked D) as template, and marker in the lane marked M. The molecular weight marker comprises DNA bands of 100, 200 and 300 bases, starting from the bottom.

As shown in exemplary figures, FIG. 5 shows results for two mammalian cell types, K562 and THP cells, treated with the effector oligonucleotides described in FIG. 4. The steps and methods used to introduce effector oligonucleotides into cells entail known methods in the art, and analogous methods exist to introduce effector oligonucleotides into other cell types. The steps relating to effector oligonucleotide-mediated recombination subsequent to introduction of effector oligonucleotides into the cells are not cell type specific. Consequently, the methods described here can be applied to additional cell types, including cell types of bacterial and eukaryotic origin, including mammalian, human, animal, plant, yeast, insect, reptilian origin. Mammalian cell types that may be used include stem cells and adult or differentiated cells of various origins. Stem cell types that may be used include embryonic stem cells, induced pluripotent stem cells, adult stem cells, hematopoietic stem cells, adult stem cells derived from or of various tissues or organs of various types, cord blood stem cells, and cancer stem cells. Additional cell types include multipotent progenitor cells, lineage-restricted progenitor cells, common myeloid progenitor cells, Granulocyte-macrophage progenitor cells, and megakaryocyte-erythroid progenitor cells. Differentiated cell types that may be used include immune cells, muscle cells, cardiac muscle cells, cells of the eye, skin cells, hair cells, epithelial cells, lung cells, kidney cells, interstitial cells, neuronal cells and any other cell type that is found in the body.

Any desired cell type may be used for the cells of the invention. The cells may be prokaryotic or eukaryotic. The cells may express the protein of interest (i.e. a protein that is to be altered by treatment with the effector oligonucleotide) in their native state or not. Eukaryotic cells that may be used include but are not limited to fungi cells such as yeast cells, plant cells and animal cells. Animal cells that can be used include but are not limited to mammalian cells and insect cells, and primary or immortalized cells derived from mesoderm, ectoderm or endoderm layers of eukaryotic organisms. The cells may be endothelial, epidermal, mesenchymal, neural, renal, hepatic, hematopoietic, or immune cells. For example, the cells may be intestinal crypt or villi cells, clara cells, colon cells, intestinal cells, goblet cells, enterochromafin cells, enteroendocrine cells. Mammalian cells that are useful in the method include but are not limited to human, non-human primate, cow, horse, goat, sheep, pig, rodent (including rat, mouse, hamster, guinea pig), marsupial, rabbit, dog and cat. The cells can be differentiated cells or stem cells, including embryonic stem cells.

Cells of the invention can be primary, transformed, oncogenically transformed, virally transformed, immortalized, conditionally transformed, explants, cells of tissue sections, animals, plants, fungi, protists, archaebacteria and eubacteria, mammals, birds, fish, reptiles, amphibians, and arthropods, avian, chicken, reptile, amphibian, frog, lizard, snake, fish, worms, squid, lobster, sea urchin, sea slug, sea squirt, fly, squid, hydra, arthropods, beetles, chicken, lamprey, ricefish, zebra finch, pufferfish, and Zebrafish.

Additionally, cells such as blood/immune cells, endocrine (thyroid, parathyroid, adrenal), GI (mouth, stomach, intestine), liver, pancreas, gallbladder, respiratory (lung, trachea, pharynx), Cartilage, bone, muscle, skin, hair, urinary (kidney, bladder), reproductive (sperm, ovum, testis, uterus, ovary, penis, vagina), sensory (eye, ear, nose, mouth, tongue, sensory neurons), Blood/immune cells such as_B cell, T cell (Cytotoxic T cell, Natural Killer T cell, Regulatory T cell, T helper cell, γδ Tcell, Natural killer cell; granulocytes (basophil granulocyte, eosinophil granulocyte, neutrophil granulocyte/hypersegmented neutrophil), monocyte/macrophage, red blood cell (reticulocyte), mast cell, thrombocyte/Megakaryocyte, dendritic cell; endocrine cells such as: thyroid (thyroid epithelial cell, parafollicular cell), parathyroid (parathyroid chief cell, oxyphil cell), adrenal (chromaffin cell), nervous system cells such as: glial cells (astrocyte, microglia), magnocellular neurosecretory cell, stellate cell, nuclear chain cell, boettcher cell, pituitary, (gonadotrope, corticotrope, thyrotrope, somatotrope, lactotroph), respiratory system cells such as pneumocyte (type I pneumocyte, type II pneumocyte), clara cell, goblet cell; circulatory system cells such as myocardiocyte.pericyte; digestive system cells such as stomach (gastric chief cell, parietal cell), goblet cell, paneth cell, G cells, D cells, ECL cells, I cells, K cells, enteroendocrine cells, enterochromaffin cell, APUD cell, liver (hepatocyte, kupffer cell), pancreas (beta cells, alpha cells), gallbladder, cartilage/bone/muscle/integumentary system cells such as osteoblast, osteocyte, steoclast, tooth cells (cementoblast, ameloblast), cartilage cells: chondroblast, chondrocyte, skin/hair cells: trichocyte, keratinocyte, melanocyte, muscle cells: myocyte, adipocyte, fibroblast, urinary system cells such as podocyte, juxtaglomerular cell, intraglomerular mesangial cell/extraglomerular mesangial cell, kidney proximal tubule brush border cell, macula densa cell; reproductive system cells such as spermatozoon, sertoli cell, leydig cell, ovum, ovarian follicle cell; sensory cells such as organ of corti cells, olfactory epithelium, temperature sensitive sensory neurons, merckel cells, olfactory receptor neuron, pain sensitive neurons, photoreceptor cells, taste bud cells, hair cells of the vestibular apparatus, carotid body cells are useful to make cells or cell lines of the invention.

Plant cells that are useful include roots, stems and leaves and plant tissues include meristematic tissues, parenchyma collenchyma, sclerenchyma, secretory tissues, xylem, phloem, epidermis, periderm (bark).

Cells that are useful for the cells and cell lines of the invention also include but are not limited to: Chinese hamster ovary (CHO) cells, established neuronal cell lines, pheochromocytomas, neuroblastomas fibroblasts, rhabdomyosarcomas, dorsal root ganglion cells, NS0 cells, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171). L-cells, HEK-293 (ATCC CRL1573) and PC12 (ATCC CRL-1721), HEK293T (ATCC CRL-11268), RBL (ATCC CRL-1378), SH-SYSY (ATCC CRL-2266), MDCK (ATCC CCL-34), SJ-RH30 (ATC CRL-2061), HepG2 (ATC HB-8065), ND7/23 (ECACC 92090903), CHO (ECACC 85050302), Vero (ATCC CCL 81), Caco-2 (ATC HTB 37), K562 (ATCC CCL 243), Jurkat (ATCC TIB-152), Per.C6 (Crucell, Leiden, The Netherlands), Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2 OS (ATCC HTB-96), T84 (ATC CCL 248), or any established cell line (polarized or nonpolarized) or any cell line available from repositories such as American Type Culture Collection (ATCC, 10801 University Blvd. Manassas, Va. 20110-2209 USA) or European Collection of Cell Cultures (ECACC, Salisbury Wiltshire SP4 0JG England).

Further, cells that are useful in the method of the invention are mammalian cells amenable to growth in serum containing media, serum free media, fully defined media without any animal-derived products, and cells that can be converted from one of these conditions to another.

II. Composition of Stem Cells and Methods for Modifying Stem Cells

The invention provides for a composition of stem cells and/or a population of stem cells that have been engineered using an effector oligonucleotide as described herein. In some instances, the stem cells have been engineered to be refractory to HIV-infection. In one example, this is accomplished by introducing a mutation in the CCR5 gene that creates a frameshift mutation. In one embodiment, the CCR5 variant has 32 bases deleted from CCR5 to create a CCR5 variant. Specifically, the Δ32 variant of CCR5 is created by a deletion of 32 bases from the gene, resulting in a frameshift mutation. This deletion occurs downstream of the start codon at a position such that the preceding 52% of CCR5 plus an additional 31 novel carboxy-terminal amino acids encoded by the frameshift mutation persist. In other embodiments, a CCR5 variant is generated such that less than 32 bases is deleted but still results in a frameshift mutation such that additional novel carboxy-terminal amino acids are encoded by the frameshift mutation.

Stem cells that are used for the invention can be obtained from different starting sources including, but not limited to, peripheral blood, cell cultures, adult or fetal tissues. The stem cells that are used for the invention for molecular manipulation are cells that have self-regeneration capacities and the ability to become another type of cell in its differentiation pathway. The stem cells that are used as a starting source can be totipotent, pluripotent, multipotent, oligopotent and/or unipotent. In some embodiments, the cells are obtained from peripheral blood. In other embodiments, a treatment is used to mobilize immune stem cells into the peripheral blood before the blood is collected, including, but not limited to, treatment with a cytokine such as G-CSF. In other embodiments, the cells are obtained from umbilical cord blood.

In other embodiments, the starting course of stem cells can be induced pluripotent stem cells (iPS cells of iPSC). As is known to one of skill in the art, iPS cells can be obtained by introduction of a cocktail of genes into or with differentiated cells. The cocktail of genes includes but is not limited to Oct 3/4, Sox2, Nanog, c-Myc and LIN-28. Alternatively, a cocktail of chemicals known to one of skill in the art, structurally related compounds, functionally related compounds or a combination thereof can be used to generate iPS cells. See, for example, Hou P., et al. *Science* Vol. 341 No. 6146 pp. 651-654; Aug. 9, 2013. In some embodiments, the piggyback transposable system is used to introduce the cocktail of genes for a traceless production of iPSC where the genes can be removed following their desired activity with no DNA foot-print or DNA residues left behind on the genome of the treated cells. See, for example, Lacoste, A., et al., *Cel Stem Cell*. 2009 Sep. 4; 5(3):332-42. doi: 10.1016/j.stem.2009.07.011.

In other embodiments, the cells are obtained from adult or fetal tissues, including an organ, the bone marrow, spleen, thymus or liver. Methods for isolating various types of stem cells from these organs are known to one of the skill in the art.

Other non-limiting examples of starting cells that can be used include: stem cells which are or are not themselves subject to infection by HIV, stem cells where the genetic locus comprising the CCR5 gene is or is not transcriptionally active in the stem cells.

In other embodiments, the stem cell types may be anyone or more of the cells in the group consisting of embryonic stem cells, induced-pluripotent stem cells, hematopoietic stem cells, corid blood stem cells, multipotent progenitor cells, lineage-restricted progenitor cells, common myeloid progenitor cells, Granulocyte-macrophage progenitor cells and megakaryocyte-erythroid progenitor cells.

In other embodiments, the stem cells that are used express one or more of the markers selected from the group consisting of: CD34, CD133, CD105, CD45, CD59, Thy1 (CD90), C-kit (CD117) and SLAM family of cell surface markers. In some embodiments, the SLAM family of cell surface markers is selected from the group consisting of CD48, CD150, and CD244. In other embodiments, the stem cells do not express one or more of the markers selected from the group consisting of: CD13, CD33, CD71, CD19, and CD61.

In other embodiments, the stem cells comprise an RNA corresponding to an intracellular, non-cell-surface-localized or a cell-surface localized stem cell marker. Additional non-limiting examples of these stem cell markers include transcription factor gene families, signal pathway genes, kinase genes. See for example, Kim Y. C., et al. *PNAS* Vol. 106(20):8278-83 (2009), the contents of which are expressly incorporated for the markers, gene expression profiles and gene signatures of $CD34^+$ hematopoietic stem cells. Non-limiting examples of transcription factor gene families include: zf-C2H2, KRAB, Homeobox, HLH, BTB, SCAN, Hormone receptor, zf-C4, bZIP, ETS, Fork head, PAS, TIG, PHD, GATA, and MYB DNA-binding. Non-limiting examples of signal pathway genes detected in $CD34^+$ hematopoietic cells include: calcium signaling pathway, ERB B signaling pathway, Hedgehog signaling pathway, JAK-STAT signaling pathway, MAPK signaling pathway, mTOR signaling pathway, Notch signaling pathway, Phosphatidylinositol signaling system, TGF-beta signaling pathway, VEGF signaling pathway, and WNT signaling pathway. Non-limiting examples of Kinase genes detected in $CD34^+$ hematopoietic cells include: AGC, Atypical, Calcium/calmodulin regulated kinases, Casein kinase, CMGC, Receptor guanylate cyclase, STE, Tyrosine kinase-like, and Tyrosine kinases. Other markers and expression profiles that can be used are disclosed in Liu, X., et. al, *J. Leukocyte Biology*, Vol 82 (4) pp 986-1002, October 2007, the contents of which are expressly incorporated for the markers, gene expression profiles and gene signatures of $CD34^+$ hematopoietic stem cells.

The starting source of stem cells includes stem cell where there is at least 1 copy of wild type CCR5. That is, the stem cells that contain at least 1 copy of CCR5 that does not have any CCR5 mutations, CCR5 deletions (e.g., resulting in a frameshift), and/or CCR5 truncation. In some cases, the stem cells contain 2 copies of wild type CCR5. In some cases, the stem cells carry one or two copies of a variant of CCR5 that encodes a protein that may act as a receptor or co-receptor for HIV docking or entry.

In addition, the starting source of stem cells includes stem cells that have the potential to become infected with HIV and/or stem cells that can differentiate into cells that could become infected with HIV. Non-limiting examples include stem cells that can become immune cells, such as $CD4^+$ T cells and $CD4^+$ stem cells.

F. Detection, Selection and/or Isolation of Cells with Effector Oligonucleotide-Mediated Editing Following treatment of cells with effector oligonucleotides designed to alter the genome of the cells, fluorogenic oligonucleotide probes in combination with fluorescence-activated cell sorting can be used to selectively detect and isolate the rare, optimally engineered cells that comprise the altered genetic sequence resulting from recombination of the mismatch sequence encoded by the effector oligonucleotide into the genome. In order to increase the signal to noise for detecting optimally-engineered cells from non-engineered cells using the fluorogenic probes directed to detect the altered sequence, effector oligonucleotides designed to introduce greater than one mismatch were tested. Effector oligonucleotides that comprise greater than a single mismatch were found to result in effector oligonucleotide-mediated alteration of the genome, an unexpected result in view of the teaching in the art that effector oligonucleotides must be essentially identical to their corresponding target sequences.

In some embodiments, following effector oligonucleotide-mediated alteration of the genome in cells, optimally-engineered cells may be detected and isolated using fluorogenic oligonucleotide probes. Exemplary methods and compositions that can be used for detection and/or isolation include US2006/147937, US2010/212040, US2009/106853, and US2012/015841 (the contents of which are expressly incorporated herein by reference for the teaching of fluorogenic oligonucleotide probes, and other compositions for detection and/or isolation of engineered cells). In some embodiments wherein the effector oligonucleotide-mediated recombination results in the expression of an altered genetic sequence following recombination events, cells having had undergone recombination may be positively detected or isolated using fluorogenic probes that are designed to detect and report the presence of the resulting expressed sequence. In some embodiments wherein the effector oligonucleotide-mediated recombination results in the expression of an altered genetic sequence following recombination events, cells having had undergone recombination may be negatively detected or isolated using fluorogenic probes that are designed to detect and report the presence of the original, non-recombined expressed sequence. In some embodiments wherein the effector oligonucleotide-mediated recombination results in the expression of an altered genetic sequence following recombination events, cells having had undergone recombination may be positively detected or isolated using fluorogenic probes that are designed to detect a target within the expressed sequence that is present in both the recombined and non-recombined sequence, but that is differentially detectable or accessible in the cells comprising the recombined sequence. In some embodiments wherein the effector oligonucleotide-mediated recombination event results in the expression of an altered genetic sequence following recombination events, cells having had undergone recombination may be negatively detected using fluorogenic probes that are designed to detect a target within the expressed sequence that is present in both the recombined and non-recombined sequence, but that is differentially detectable or accessible in the cells comprising the non-recombined sequence. In some embodiments wherein the effector oligonucleotide-mediated recombination event results in the increased expression of a genetic sequence, cells having had undergone recombination may be positively detected using fluorogenic probes that are designed to detect and report the presence of the resulting expressed sequence, wherein cells with an increased signal for the probe would be identified. In some embodiments wherein the effector oligonucleotide-mediated recombination event results in the decreased expression of a genetic sequence, cells having had undergone recombination may be negatively detected using fluorogenic probes that are designed to detect and report the presence of the resulting expressed sequence, wherein cells with a decreased signal for the probe would be identified.

In any of the examples above, cells that are positively or negatively detected may be isolated, for instance using fluorescence-activated cell sorting. The isolated cells may be isolated individually or in batch or pools. The isolated cells may be expanded in culture clonally, or in pool or batch. The resulting expanded cell culture can be further processed to remove the culture media from the resulting cells, and the cells can be resuspended in a suitable media for use in cell therapy.

Cells treated with the effector oligonucleotides or the cells that are isolated cells or the cells expanded from the isolated cells may be subjected to downstream analysis, including PCR, genomic PCR, RT-PCR, DNA sequencing, whole-genome sequencing, in situ hybridization, immunofluorescence, western blotting, functional assays, kinetic assays, or any other downstream testing that is known in the art to study and characterize cells or sub-cellular fractions and preparations. Cells treated with the effector oligonucleotides, the isolated cells, or the cells expanded from the isolated cells may be used for cell therapy or to prepare preparations of therapeutic cells or cellular reagents for cell therapy applications. Cells treated with the effector oligonucleotides, the isolated cells, the cells expanded from the isolated cells or preparations of any of these may be introduced into humans or animals for testing or therapeutic applications.

One or more of the downstream testing methods may be used to test the cells treated with effector oligonucleotides, the isolated cells or the cells expanded from the isolated cells for the altered or mismatched sequence encoded by the effector oligonucleotides used to treat the cells. For instance, PCR or DNA or genomic sequencing may be used for this purpose. In addition, PCR or DNA or genomic analysis including whole-genome analysis or sequencing may be used to test for the presence of any unintended off-target activity or genome modification following treatment with effector oligonucleotide. This testing can be applied to cells expanded from individually isolated effector oligonucleotide-treated cells or effector oligonucleotide-treated cells isolated as a pool or batch. Cell or cell preparations that are confirmed to comprise the intended genomic modification introduced by the effector oligonucleotide and a low frequency of or no other alteration of the genome could be identified. These cells could be used in downstream applications, including cell therapy, where they may be expected to result in a greater likelihood of efficacy and deceased likelihood of side-effects or adverse unintended effects due to off-target or unintended modification of the genome.

FIG. 4A and Example 3 below describe a series of effector oligonucleotides each of which comprises a mismatch greater than one base and that were used or can be used to treat cells to introduce a genomic alteration. Multiple oligos were detected as producing the intended genomic alteration in a portion of the cells that were treated. This set of oligos was targeted to introduce an alteration within the CCR5 gene. Oligos may also be designed to introduce genomic alterations in other genes or DNA sequences, including non-coding sequences such as promoters, gene-regulatory elements and DNA binding sites. Any gene or DNA sequence may be targeted according to the methods described.

G. CCR5 Deletion and Populations of Stem Cells with Modified CCR5

Figure 6:
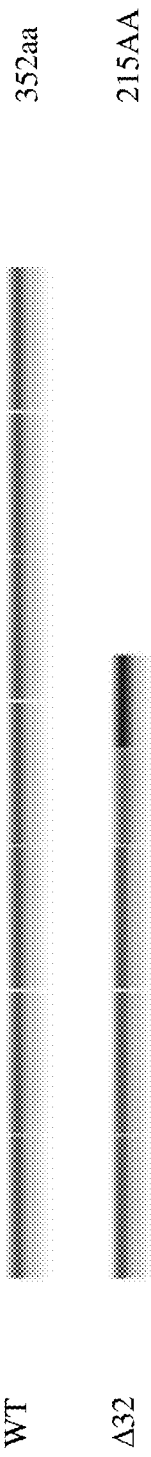
FIG. 6 depicts a schematic of the amino acid (AA) sequences of the wild-type (WT) and Δ32 variants of CCR5. The total number of amino acids for each variant is indicated.

The modified stem cells of this invention have an altered CCR5 such that there is a frameshift mutation. One exemplary embodiment is shown in FIG. 1 of a mutation where 32 bases of the CCR5 are deleted (bold underlined sequence in FIG. 1). This is also referred to as "delta-32 deletion" or "Δ32 deletion". The 32 bases that are deleted have the sequence of: 5'-GTCAGTATCAATTCGGAAGAAT-TTCCAGACA (SEQ ID NO:4). Other frameshift mutations are contemplated within the scope of the invention, for example, those where 29 bases, 26 bases, etc. are removed such that it results in a frameshift and where novel carboxy-terminal amino acids are added as exemplified in FIG. 6. In some embodiments, mutations that result in one or more stop codon are excluded from specific embodiments of the invention.

Oligonucleotides can be used to modify the wild-type variant of CCR5 into the Δ32 variant of CCR5 in the genome of stem cells. These oligonucleotides are optimized for delivery into stem cells. Considerations for optimization include, but are not limited to, (i) oligonucleotides should be non-toxic and compatible with cell viability, (ii) achieve delivery of a concentration of oligonucleotide into cells that results in a precise modification of CCR5, (iii) are fully-defined and amenable to quality control and further optimization, and (iv) yield stem cells where the ability of the isolated stem cells to give rise to cells of the immune system is not perturbed. Exemplary oligonucleotides that can be used are described in greater details in the Examples section.

In some embodiments, stem cells that are used have been manipulated (e.g. by induction) such that they transiently express CCR5 in immune stem cells without loss of the stem cell function. The induction of expression of the CCR5 locus in immune stem cells can be helpful when detection tools, such as molecular beacon probes (e.g., Chromovert® probes) are used to detect cells comprising the Δ32 CCR5.

Utilizing the methodology described herein, one of skill in the art can modify the CCR5 sequence in stem cells to create a population of modified or recombinant stem cells containing CCR5 modifications (e.g., Δ32 deletion) such that it is rendered refractory to HIV infection. Cells that differentiate from these stem cells are also rendered refractory to HIV infection. It is understood that reference to a population of cells described herein contemplates and includes isolated populations.

In some embodiments, the invention provides for compositions comprising a substantially pure population of recombinant stem cells, wherein the stem cells comprise a Δ32 deletion in a CCR5 gene. The deletion can be in one allele or both alleles. In one embodiment, the Δ32 deleted sequence is SEQ ID NO:4.

The invention provides for homogeneous or substantially pure populations of recombinant stem cells that contain the Δ32 CCR5 deletion and compositions comprising these populations. Accordingly, in some embodiments, the population contains at least about 5% of the stem cell in the population with the Δ32 deletion. In other embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the stem cell in the population with the Δ32 deletion. In some embodiments, at least about includes an upper limit of about 100%, 99%, 98%, 97%, 96%, 95%, 94%, 93%, 92%, 91%, or 90%, e.g. at least about 50% is about 50% to 90%, 50% to 91%, 50% to 92%, 50% to 93%, 50% to 94%, 50% to 95%, 50% to 96%, 50% to 97%, 50% to 98%, 50% to 99%, or 50% to 100%.

The homogeneous or substantially pure populations of recombinant stem cells that contain the Δ32 CCR5 deletion can be further characterized by its markers (intracellular and extracellular). The stem cells can express one or more markers selected from the group consisting of: CD34, CD133, CD105, CD45, CD59, Thy1/CD90, C-kit (CD117) and SLAM family of cell surface markers or a combination thereof. In some embodiments, the SLAM family of cell surface markers is selected from the group consisting of CD48, CD150, and CD244. In other embodiments, the stem cells do not express one or more of the markers selected from the group consisting of: CD13, CD33, CD71, CD19, and CD61.

In other embodiments, the stem cells comprise an RNA corresponding to an intracellular, non-cell-surface-localized or a cell-surface localized stem cell marker. Additional non-limiting examples of these stem cell markers include transcription factor gene families, signal pathway genes, kinase genes. Non-limiting examples of transcription factor gene families include: zf-C2H2, KRAB, Homeobox, HLH, BTB, SCAN, Hormone receptor, zf-C4, bZIP, ETS, Fork head, PAS, TIG, PHD, GATA, and MYB DNA-binding. Non-limiting examples of signal pathway genes detected in $CD34^+$ hematopoietic cells include: calcium signaling pathway, ERB B signaling pathway, Hedgehog signaling pathway, JAK-STAT signaling pathway, MAPK signaling pathway, mTOR signaling pathway, Notch signaling pathway, Phosphatidylinositol signaling system, TGF-beta signaling pathway, VEGF signaling pathway, and WNT signaling pathway. Non-limiting examples of Kinase genes detected in $CD34^+$ hematopoietic cells include: AGC, Atypical, Calcium/calmodulin regulated kinases, Casein kinase, CMGC, Receptor guanylate cyclase, STE, Tyrosine kinase-like, and Tyrosine kinases. Other markers and expression profiles that can be used are disclosed in Liu, X., et. al, *J. Leukocyte Biology*, Vol 82 (4) pp 986-1002, October 2007, the contents of which are expressly incorporated for the markers, gene expression profiles and gene signatures of $CD34^+$ hematopoietic stem cells.

Accordingly, in some embodiments, the population contains at least about 5% of the stem cell in the population with the one or more marker profile (or combination of marker) described above. In other embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the stem cell in the population with the one or more marker (or combination of marker) profile described above. In some embodiments, at least about includes an upper limit of about 100%, 99%, 98%, 97%, 96%, 95%, 94%, 93%, 92%, 91%, or 90%, e.g. at least about 50% is about 50% to 90%, 50% to 91%, 50% to 92%, 50% to 93%, 50% to 94%, 50% to 95%, 50% to 96%, 50% to 97%, 50% to 98%, 50% to 99%, or 50% to 100%.

Various methods can be used to obtain a substantially pure or homogeneous population of modified stem cells. Detection tools such as those involving labels or fluorescence probes (e.g., fluorophores, quenchers, molecular beacon probes and the like) can be used to select for the stem cells that have the Δ32 modification. One non-limiting example of a system that can be used in conjunction with the stem cells is the Chromovert® technology (see, e.g., U.S. Pat. No. 6,692,965). The Chromovert® technology can be used to rapidly isolate and purify the stem cells that have modified CCR5 (e.g, Δ32 CCR5 deletion). This technology can be used with the optimized probes to detect and isolate immune stem cells that comprise the Δ32 variant of CCR5 are established, where the conditions: (i) provide the highest signal to noise for Δ32 versus wild-type CCR5, (ii) are compatible with detection and isolation of viable cells, and (iii) yield immune stem cells where the ability of the isolated stem cells to give rise to cells of the immune system is not perturbed.

One of skill in the art will appreciate that other methods exist to obtain and/or detect substantially pure or homogeneous population of modified cells, such as stem cells. For example, fluorescence-activated cell sorting (FACS) can be used to select for specific stem cells using positive staining or alternatively, to exclude by negative staining (e.g., to discard population of stem cells which are negative for CCR5).

The stem cells of the invention can give rise to all cells of the immune system or they can give rise to myeloid (monocytes, macrophages, neutrophils, basophils, eosinophils, erythrocytes, megakaryocytes, platelets, dendritic cells) or lymphoid lineages (T-cells, B-cells, NK-cells). In some embodiments, the stem cells can be myeloid-biased, lymphoid-biased or unbiased with respect to the differentiated cell types that may be derived from the stem cells.

In some embodiments, the stem cells are modified and allowed to differentiate into the immune cell types that are normally subject to infection by HIV. With the modifications described herein, these stem cells and differentiated cells derived from the stem cells may be used according to the invention to produce corresponding cell types or immune cell types that are resistant to infection by HIV. In one embodiment, the differentiated cell type is an immune T-cell. In another embodiment, the differentiated cell type is a cell type wherein the genetic locus comprising the CCR5 gene is or is not transcriptionally active. In some embodiments, the resulting treated differentiated cells may be trans-differentiated or dedifferentiated into other cell types including into stem cell types for subsequent testing or therapeutic use. In one embodiment, the treated cells of the method may be dedifferentiated into hematopoietic stem cells.

H. Methods of Treating Individuals with Recombinant Cells Produced by Effector Oligonucleotide-Mediated Alteration The population of modified cells (i.e. recombinant cells) as described herein can be expanded by standard cell culture for cells that are known to one of the skill in art. The population of modified cells can be mixed with a pharmaceutically acceptable carrier to create a pharmaceutical composition suitable for cell therapy. The pharmaceutical composition comprising modified cells, such as stem cells, as described herein, include at least one pharmaceutically acceptable adjuvant and/or excipient, as are well known to those skilled in the art. The population of modified cells can be tested in non-human animal models of the disease to be treated to determine the effective amount or range of effective amount of modified cells that can be used. Non-human animal models can also be used to evaluate the retention of cell function by the population of modified cells.

As a non-limiting example, a population of modified stem cells as described herein can be expanded by standard cell culture for stem cells that are known to one of the skill in art. The population of modified stem cells can be mixed with a pharmaceutically acceptable carrier to create a pharmaceutical composition suitable for cell therapy. The population of modified stem cells can be tested in non-human animal models of HIV to determine the effective amount or range of effective amount of modified stem cells that can be used. Non-human animal models of HIV can also be used to evaluate the retention of stem cell function by the population of modified stem cells.

As noted above, the stem cells can differentiate into one or more cell types, in particular, when introduced in vivo and exposed to the biological milieu of growth factors, cytokines and other biological factors that would induce a stem cell to differentiate. Without being bound by theory, the population of modified stem cells can self-renew to generate an endless supply of modified stem cells as well as differentiate into cells that are refractory to HIV infection. Examples of such differentiated cells include, but are not limited to, immune cell types that are normally otherwise subject to infection by HIV. In one embodiment, the differentiated cell type is an immune T-cell. In another embodiment, the differentiated cell type is a cell type wherein the genetic locus comprising the CCR5 gene is or is not transcriptionally active.

In addition, the population of modified cells (e.g. stem cells) can be tested to determine the genomic integrity and to assess if there are any unintended (and/or undesired) genomic modifications. One of the skill in the can use any molecular biology techniques to detect and measure the frequency of aberrant genome modification. This assessment can be important to ascertain the safety of cell therapy using various populations of modified cells, such as modified stem cells.

The population of modified stem cells can be tested to determine if certain cohorts of individuals provide cells that comprise ideal characteristics for successful cell therapy. Non-limiting examples of characteristics that can be assessed include: markers (intracellular and extracellular), longevity in cell culture, renewal potential, expansion rate, gene expression profiles, proteomics and functionality (e.g., ability to differentiate into certain types of cells).

Analysis of the characteristics of populations of stem cells from certain cohorts may be beneficial when designing treatment plans, including using the cell therapy as primary treatment as well as using it to aid in the treatment of HIV infection. Certain patent sub-populations can be identified as being particularly receptive to treatment with a population of modified stem cells.

I. Methods of Treating Individuals with Effector Oligonucleotides

In human or animal cell therapy applications, preferred genetic sequences that may be selected to serve as targets for effector oligonucleotide-mediated alteration of the genome include sequences implicated in disease or infection, or susceptibility to disease or infection. In particular, genetic sequences or variations of two or more bases that produce disease or result in susceptibility to a disease or infection would be preferred target sequences for modification by effector oligonucleotide-mediated recombination. Examples of such sequences include the CCR5 gene or locus, where alteration of the wild-type sequence in cells of the immune system from individuals comprising wild-type CCR5 can be used as part of a cell therapy for HIV/AIDS. The alteration of CCR5 can be designed to mimic, replicate or approximate the Δ32 sequence variant of CCR5. Numerous diseases or infections or susceptibilities to disease or infection exist that result from one or more known DNA variations or mutations. These sequences represent preferred targets for alteration using effector oligonucleotide-mediated recombination.

The effector oligonucleotides can also be used to treat a subject in need thereof, i.e. rather than treating a subject by cell therapy methods using a recombinant cell that has been altered by treatment with an effector oligonucleotide, the effector oligonucleotide can be administered to the subject to mediate the alteration of target cells within the subject. The invention provides for the use of an effector oligonucleotide to correct, alter or eliminate the sequence associated with a disease or infection or susceptibility to the disease or infection, wherein the effector oligonucleotide is targeted to a variant of a gene or portion thereof, that is linked or associated with a disease or infection or susceptibility to a disease or infection. As such, the invention provides for a method of treating a disease or infection, or susceptibility to the disease or infection, in a subject comprising administering to the subject in need thereof an effective amount of an effector oligonucleotide. In some embodiments of the method of treating a disease or infection in a subject, the effector oligonucleotide is targeted to a variant of a gene or portion thereof, that is linked or associated with the disease or infection.

J. Pharmaceutically Acceptable Compositions

The effector oligonucleotides for use in the methods of treatment as described herein, e.g. treatment by administering the one or more effector oligonucleotides as disclosed herein, can be administered in the form of pharmaceutical compositions. These effector oligonucleotides and pharmaceutical compositions thereof can be administered by a variety of routes including oral, rectal, cerebrospinal, transdermal, subcutaneous, topical, transmucosal, nasopharangeal, pulmonary, intravenous, intraperitonial, intramuscular, and intranasal. In some embodiments, the effector oligonucleotides are administered systemically, wherein the administration is intravenous or intraperitoneal administration.

Thus, provided herein are pharmaceutical compositions which contain, as the active ingredient, one or more of the effector oligonucleotides as described herein associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In another aspect, one or more effector oligonucleotides as described herein are encapsulated within a microcarrier for deliver to an individual. In some embodiments the microcarrier encapsulates more than one effector oligonucleotide species. In some embodiments, the one or more effector oligonucleotide species encapsulated within the microcarrier comprises a nucleic acid sequence selected from the group consisting of SEQ ID NOs:5-37. Methods of encapsulating oligonucleotides in microcarriers are well known in the art, and described, for example, in International application WO98/55495. Colloidal dispersion systems, such as microspheres, beads, macromolecular complexes, nanocapsules and lipid-based system, such as oil-in-water emulsions, micelles, mixed micelles and liposomes can provide effective encapsulation of oligonucleotides within microcarrier compositions. The encapsulation composition may further comprise any of a wide variety of components. These include, but are not limited to, alum, lipids, phospholipids, lipid membrane structures (LMS), polyethylene glycol (PEG) and other polymers, such as polypeptides, glycopeptides, and polysaccharides.

In some embodiments, the compositions can be formulated in a unit dosage form, each dosage containing from about 1 mg to about 1000 mg or more, such as any of about 1 mg to about 900 mg, about 1 mg to about 800 mg, about 1 mg to about 700 mg, about 1 mg to about 600 mg, about 1 mg to about 500 mg, about 5 mg to about 1000 mg, about 5 mg to about 900 mg, about 5 mg to about 800 mg, about 5 mg to about 700 mg, about 5 mg to about 600 mg, or about 5 mg to about 500 mg, inclusive, including any range in between these values, of the active ingredient, i.e. one or more effector oligonucleotides. In some embodiments, the compositions can be formulated in a unit dosage form, each dosage containing from about 1 µg to about 1000 µg or more, such as any of about 1 µg to about 900 µg, about 1 µg to about 800 µg, about 1 µg to about 700 µg, about 1 µg to about 600 µg, about 1 µg to about 500 µg, about 5 µg to about 1000 µg, about 5 µg to about 900 µg, about 5 µg to about 800 µg, about 5 µg to about 700 µg, about 5 µg to about 600 µg, or about 5 µg to about 500 µg, inclusive, including any range in between these values, of the active ingredient, i.e. one or more effector oligonucleotides. The term "unit dosage forms" refers to physically discrete units suitable as unitary dosages for subjects, each unit containing a predetermined quantity of active material calculated to produce the desired therapeutic effect, in association with a suitable pharmaceutical excipient or carrier.

The therapies disclosed herein are effective over a wide dosage range and are generally administered in a therapeutically effective amount. It will be understood, however, that the amount of the effector oligonucleotide actually administered will be determined by a physician, in the light of the relevant circumstances, including the condition to be treated, the chosen route of administration, the actual compound administered, the age, weight, and response of the individual subject, the severity of the subject's symptoms, and the like.

For preparing solid compositions such as tablets, the effector oligonucleotide is mixed with a pharmaceutical excipient or carrier to form a solid preformulation composition containing a homogeneous mixture of an effector oligonucleotide of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the effector oligonucleotide from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Parenteral routes of administration include but are not limited to direct injection into a central venous line, intravenous, intramuscular, intraperitoneal, intradermal, or subcutaneous injection. Formulations suitable for parenteral administration (e.g., an effector oligonucleotide as described herein in a microcarrier formulation) are generally formulated in USP water or water for injection and may further comprise pH buffers, salts bulking agents, preservatives, and other pharmaceutically acceptable excipients. Effector oligonucleotides as described herein, for example as microcarrier complexes or encapsulates, for parenteral injection may be formulated in pharmaceutically acceptable sterile isotonic solutions such as saline and phosphate buffered saline for injection.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described herein. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

K. Articles of Manufacture and Kits

The invention also provides kits and articles of manufactures for use in the instant methods. Kits of the invention include one or more containers comprising one or more effector oligonucleotides as described herein and instructions for use in accordance with any of the methods of the invention described herein.

In some embodiments, these instructions comprise a description of administration of the effector oligonucleotides for treating HIV infection, AIDS, or any disease where a genetic variation of two or more bases causes or is associated with the disease or susceptibility to the disease or infection. The kit may further comprise a description of selecting cells or an individual suitable for treatment based on identifying whether the cells or that individual has the disease and the stage of the disease or the susceptibility to the infection.

The instructions relating to the use of the effector oligonucleotides can generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert can indicate that the composition is used for treating susceptibility to HIV infection, HIV infection, AIDS, or any disease where a genetic variation of two or more bases causes or is associated with the disease or any other uses described herein. Instructions may be provided for practicing any of the methods described herein.

The kits of this invention are in suitable packaging. Suitable packaging includes, but is not limited to vials, bottles, jars, flexible packaging (e.g., sealed Mylar or plastic bags), and the like. Also contemplated are packages for use in combination with a specific device, such as syringe, pre-filled syrine, electroporation cuvetter, an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an effector oligonucleotide as described herein. The container may further comprise a second pharmaceutically active agent. The kit may comprise components suitable for treating cells to prepare cells with therapeutic potential, including components to isolate the cells to be treated from an individual to be treated or a donor individual, components to contact the cells with effector oligonucleotide, and components for use in the detection and isolation of cells treated with the effector oligonucleotide to comprise sequence encoded by the effector oligonucleotide. The components of the kit may include buffers and reagents for electroporation, fluorescence-activated cell sorting and for the culture and expansion of cells.

Kits may optionally provide additional components such as buffers and interpretive information. Normally, the kit comprises a container and a label or package insert(s) on or associated with the container.

Throughout this specification, various patents, patent applications and other types of publications (e.g., journal articles) are referenced. The disclosure of all patents, patent applications, and publications cited herein are hereby incorporated by reference in their entirety for all purposes.

The invention can be more fully further understood by reference to the following examples, which are provided by way of illustration and are not meant to be limiting of the scope of the invention. All citations throughout the disclosure are hereby expressly incorporated by reference.

EXAMPLES

Example 1: Electroporation of Effector Oligonucleotides into THP or K562 Cells THP or K562 cells were cultured to a maximum density of $2 \times 10^6$ per mL in RPMI culture medium (Gibco CAT 61870-036)) supplemented with 10% FBS (SAFC Biosciences CAT 12103C-500ML). The cells were rinsed with serum-free RPMI and resuspended at either $10 \times 10^6$ or $5 \times 10^6$ cells/mL. Effector oligonucleotides tested were numbers 1-8, 19 and 20 of FIG. 4A. For each reaction, 10 μL of a 3.2 μM stock solution of the effector oligonucleotide tested and 7 μL of a stock solution of 100 μM PNA reagent was added to 100 μL of the K562 and THP cells at either concentration was added to one well of 96-well electroporation plate (Biorad CAT 1652681). The PNA used here was the previously described PNA "tcPNA-679" (N-Lys-Lys-Lys-JTJTTJTTJT-OOO-TCTTCTTCTCATTTC-Lys-Lys-Lys-C) (SEQ ID NO:58). The samples were incubated on ice for 30-60 minutes, pulsed one time at 350 volts for 12 MS using the GenePulser MXCell (Biorad) and then incubated again on ice for 15-30 minutes before they were transferred into wells of a 12-well tissue culture dish using 500 μL of culture medium and incubated in a tissue culture incubator at 37° C., 5% $CO_2$. Genomic DNA was prepared from the samples after 2-3 days (Molecular Cloning Protocol: A Laboratory Manual, Volume 1, Sambrook and Russel, pp. 6.28-6.33) for analysis by PCR.

Example 2: Genomic PCR on Recombinant THP or K562 Cells

PCR was used to amplify a portion of CCR5 genomic DNA purified from treated cells of Example 1. The forward and reverse primer used were ATCACTTGGGTGGTGGCTGTGTTTGCGTCTC (SEQ ID NO:59) for the forward primer and AGTAGCA-GATGACCATGACAAGCAGCGGCAG (SEQ ID NO:60) for the reverse primer. The PCR conditions included a first step of 95° C. for 5 minutes, and 45 to 50 cycles of the following three steps: 1) 95° C. for 30 seconds, 2) 65° C. for 30 seconds, and 3) 72° C. for 20 seconds. 20 μl PCR reactions were set up for each sample and overlaid with a drop of mineral oil. Taq DNA polymerase was used with components at concentrations according to manufacturer's instructions (Roche, CAT 4738225001). A PCR product with a size of approximately 193 bases was expected for genomic sequence corresponding to wild-type CCR5 and a PCR product with a size of approximately 161 bases was expected for genomic sequence corresponding to the Δ32 variant of CCR5. FIG. 5 shows the results for K562 cells (top set of lanes) or THP cells (bottom set of lanes), with control wild type (lane 1) or deleted CCR5 (lane 2) with molecular weight marker (lane 3) shown separately on the bottom center gel. The lanes are labelled across the top with the effector oligonucleotide number (see FIG. 4A) or control (C, no effector oligonucleotide added) or marker (M). Lanes 1-10 for both the top and bottom show effector oligonucleotides 1-8, 19 and 20, respectively, with lane 11 as no effector control, and lane 12 as molecular weight marker. Lanes 13-22 for both the top and bottom show effector oligonucleotides 1-8, 19 and 20, respectively, with lane 1 as no effector control. The top samples (K562 cells) are at a density of ~4.3×10$^6$ cells/mL in lanes 1-10 and ~8.6×10' cells/mL in lanes 13-22, while the bottom samples (THP cells) are at a density of ~4.3×10$^6$ cells/mL in lanes 13-22 and ~8.6×10$^6$ cells/mL in lanes 1-10. The doublet band near the 200 MW marker show that both the wild type CCR5 and the Δ32 deleted CCR5 are present in the samples treated with effector oligonucleotides.

Example 3: Effector Oligonucleotides and Methods to Create Δ32 CCR5 in Immune Stem Cells This example describes various optimized oligonucleotides that are used to modify the wild-type variant of CCR5 into the Δ32 variant of CCR5 in the genome of immune stem cells. Exemplary oligonucleotides are shown in FIG. 4A.

Conditions that optimize the delivery of the oligonucleotides into immune stem cells are established. The conditions are that oligonucleotides: (i) are non-toxic and compatible with cell viability, (ii) achieve delivery of a concentration of oligonucleotide into cells that results in a precise modification of CCR5, (iii) are fully-defined and amenable to quality control and further optimization, and (iv) yield immune stem cells where the ability of the isolated stem cells to give rise to cells of the immune system is not perturbed.

In addition to immune stem cells, immortalized immune cell lines (including, but not limited to THP and K562 cells) are used as a proxy for immune stem cells. Identification of conditions that apply across all these cell types indicates broad applicability of the methods. Genomic PCR of DNA isolated from cells treated using test oligonucleotide and electroporation conditions are used to evaluate their effectiveness (See Examples 1 and 2).

The following effector oligonucleotides are tested in addition to the above:

```
Key to modifications, oligonucleotides are 5' to
3'.:
BNA (bridged nucleic acids) - indicated with base
underlined
6-Thio-2'-deoxyguanosine - indicated by lower
case g
8-Amino-2'-deoxyadenosine - indicated by lower
case a
                                       (SEQ ID NO: 17)
1) GAAGGTCTTCATTACACCTGCAGCTCTCATTTTCCATACATTAAAGA

TAGTCATCTTGGGGCTGGTCCTGCCGCTGCTTG (SEQ ID NO: 18)
2) GAAGGTCTTCATTACACCTGCAGCTCTCATTTTCCATACATTAAAGA

TAGTCATCTTGGGGCTGGTCCTGCCGCTGCTTG (SEQ ID NO: 19)
3) GAAGGTCTTCATTACACCTGCAGCTCTCATTTTCCATACATTAAAGA

TAGTCATCTTGGGGCTGGTCCTGCCGCTGCTTG (SEQ ID NO: 20)
4) GAAGGTCTTCATTACACCTGCAGCTCTCATTTTCCATACATTAAAGA

TAGTCATCTTGGGGCTGGTCCTGCCGCTGCTTG (SEQ ID NO: 21)
5) gAAggTCTTCATTACACCTGCAGCTCTCATTTTCCATACATTAAAGA

TAGTCATCTTGGGGCTGGTCCTGCCGCTGCTTG (SEQ ID NO: 22)
6) gaaggTCTTCATTACACCTGCAGCTCTCATTTTCCATACATTAAAGA

TAGTCATCTTGGGGCTGGTCCTGCCGCTGCTTG (SEQ ID NO: 23)
7) gAAggTCTTCATTACACCTGCAGCTCTCATTTTCCATACATTAAAGA

TAGTCATCTTGGGGCTGGTCCTGCCgCTgCTTG (SEQ ID NO: 24)
8) gaaggTCTTCATTACACCTGCAGCTCTCATTTTCCATACATTAAAGA

TAGTCATCTTGGGGCTGGTCCTGCCGCTGCTTG (SEQ ID NO: 25)
9) GAAGGTCTTCATTACACCTGCAGCTCTCATTTTCCATACATTAAAGA

TAGTCATCTTGGGGCTGGTCCTGCCGCTGCTTGTCATGGTCATCTGC

TACTCG (SEQ ID NO: 26)
10) GAAGGTCTTCATTACACCTGCAGCTCTCATTTTCCATACATTAAAGA

TAGTCATCTTGGGGCTGGTCCTGCCGCTGCTTGTCATGGTCATCTGC

TACTCG (SEQ ID NO: 27)
11) GAAGGTCTTCATTACACCTGCAGCTCTCATTTTCCATACATTAAAGA

TAGTCATCTTGGGGCTGGTCCTGCCGCTGCTTGTCATGGTCATCTGC

TACTCG (SEQ ID NO: 28)
12) GAAGGTCTTCATTACACCTGCAGCTCTCATTTTCCATACATTAAAGA

TAGTCATCTTGGGGCTGGTCCTGCCGCTGCTTGTCATGGTCATCTGC

TACTCG (SEQ ID NO: 29)
13) GAAGGTCTTCATTACACCTGCAGCTCTCATTTTCCATACATTAAAGA

TAGTCATCTTGGGGCTGGTCCTGCCGCTGCTTGTCATGGTCATCTGC

TACTCG (SEQ ID NO: 30)
14) GAAGGTCTTCATTACACCTGCAGCTCTCATTTTCCATACATTAAAGA

TAGTCATCTTGGGGCTGGTCCTGCCGCTGCTTGTCATGGTCATCTGC

TACTCG (SEQ ID NO: 31)
15) GAAGgTCTTCaTTaCACCTGCAGCTCTCATTTTCCATACATTAAAGA

TAGTCATCTTGGGGCTGGTCCTGCCGCTGCTTGTCATggTCaTCTgC

TaCTCG
```

-continued 16) gaaggTCTTCaTTaCACCTGCAGCTCTCATTTTCCATACATTAAAGA
    TAGTCATCTTGGGGCTGGTCCTGCCGCTGCTTGTCATggTCaT<u>C</u>TgC
    Ta<u>CTC</u>g
    (SEQ ID NO: 32)

17) gaaggTCTTC<u>ATTA</u>CACCTGCAGCTCTCATTTTCCATACATTAAAGA
    TAGTCATCTTGGGGCTGGTCCTGCCGCTGCTTGTCATggTCaTCTG<u>C</u>
    <u>TA</u>CTCg
    (SEQ ID NO: 33)

18) <u>GAAGG</u>TCTTCATTACACCTGCAGCTCTCATTTTCCATACATTAAAGA
    TAGTCATCTTGGGGCTGGTCCTGCCGCTg<u>C</u><u>TT</u>gTCaTggTCa<u>TC</u>TGC
    <u>TA</u>CTCg
    (SEQ ID NO: 34)

19) <u>GAAGGTCTTC</u>ATTACACCTGCAGCTCTCATTTTCCATACATTAAAGA
    TAGTCATCTTGGGGCTGGTCCTGCCGCTg<u>C</u><u>TT</u>gTCaTggTCa<u>TC</u>TGC
    <u>TA</u>CTCg
    (SEQ ID NO: 35)

20) <u>GAAGGTCTTC</u>ATTACACCTGCAGCTCTCATTTTCCATACATTAAAGA
    TAGTCATCTTGGGGCTGGTCCTGCC<u>GCTGCTTG</u>TCATGGTCAT<u>C</u>TGC
    TACTCG
    (SEQ ID NO: 36)

21) <u>GAAGG</u>TCTTC<u>ATTA</u>CACCTGCAGCTCTCATTTTCCATACATTAAAGA
    TAGTCATCTTGGGGCTGGTCCTGCC<u>GCTG</u>CTTGTCATG<u>GTCA</u>TCTGC
    TACTCG
    (SEQ ID NO: 37)

Example 4—Detecting and Isolating Immune Stem Cells Treated to Comprise Δ32 CCR5

This example describes using optimized molecular beacon probes (including, but not limited to Chromovert® probes) to detect and isolate immune stem cells comprising Δ32 CCR5 created as a result of Examples 1 and 2, or similarly treated with effector oligonucleotides of Example 3. This example uses the Chromovert® technology as a specific embodiment, but those skilled in the art will recognize, or be able to ascertain using no more than routine experimentation, other equivalents to the specific embodiment and methods discussed herein.

Chromovert® conditions for using the optimized probes to detect and isolate immune stem cells that comprise the Δ32 variant of CCR5 are established, where the conditions: (i) provide the highest signal to noise for Δ32 versus wild-type CCR5, (ii) are compatible with detection and isolation of viable cells, and (iii) yield immune stem cells where the ability of the isolated stem cells to give rise to cells of the immune system is not perturbed.

In addition to immune stem cells, immortalized immune cell lines (including, but not limited to THP and K562 cells) are used as a proxy for immune stem cells. Optimal Chromovert® probes and conditions are determined by applying test probes and methods to a mixture of cells comprising either Δ32 or wild-type variants of CCR5, isolating positive cells, and using genomic and RT-PCR methods to assess for any enrichment of cells expressing the Δ32 variant of CCR5.

The Chromovert® probes are developed by iterative rounds of testing starting with design and testing of a first set of probes. The probes are designed to correspond to the sequence and be specific for the Δ32 variant of CCR5. Specifically, the loop portion of the probe is designed to hybridize to the branch-point sequence within the sequence of the Δ32 variant of CCR5 that juxtaposes the bases upstream and downstream of the 32-base deletion. In addition, probes are designed to detect portions of CCR5 sequence that are predicted to be accessible for probe-binding only in the context of the sequence of Δ32 variant of CCR5 but not in the context of the sequence of wild-type CCR5. Such probes are synthesized and tested by using cells treated to express either the Δ32 or wild-type variant of CCR5 and those probes that produce the highest signal to noise ratios are identified. It is known that CCR5 has two alternative 5' un-translated regions. Probes that can detect the Δ32 variant of CCR5 comprising either 5' un-translated region are identified and prioritized for further optimization.

The following parameters are used for probe selection: (i) length of loop and/or stem and (ii) incorporation and extent of one or more chemically-modified bases in the loop and/or stem. Other parameters and conditions used for developing and optimizing molecular beacon probes are optionally pursued for developing Chromovert® probes that can detect the Δ32 sequence at the DNA level.

Chromovert® conditions are developed and optimized for immune stem cells, including immortalized immune cell lines. Electroporation methods are optimized for this application and specific cell types. The following parameters are used for optimizing the electroporation methods: (i) voltage and duration of electroporation, (ii) number of pulses, (iii) electroporation buffer, (iv) temperature, (v) concentration of cells, (vi) concentration of oligonucleotide, and (vii) addition of reagents that may improve the efficiency of the overall process, including DMSO and other solvents. As those skilled in the art will recognize, other parameters and conditions may also be used if necessary.

The following exemplary probes will be used and tested for further optimization. The length will vary, as will chemical composition, for instance by incorporation of one or more of the following non-limiting lists of modifications at various positions within the oligo (other chemical modifications may be used as discussed herein below or known in the art).

Key to modifications, oligonucleotides are 5' to 3':
BNA (bridged nucleic acids)—indicatedwithbaseunderlined
7-Deaza-8-aza-2'-deoxyadenosine—indicated by lower case a (in probes B15-B18)
5-Propynyl-2'-deoxyuridine—indicated by lower case t (in probes in B15-B19)
2'-Deoxyisoguanosine—indicated by lower case g (in probes B15-B17)
Probe with no modifications: 5'-GCGAGGACTATCTT-TAATGTATGGAAAATCTCGC (SEQ ID NO:38), where the bases in bold target the Δ32-CCR5 recombinant sequence (the bases at termini, i.e. not bold, comprise the stem):
  the bases in the stem may be substituted with other sequences
  the targeting sequence may correspond to another sequence specific to Δ32, for instance it may be longer, shorter, or to a different portion of the region spanning the 32 base deletion, or it may be to a sequence within the sequence of CCR5 that also exists in the Δ32 variant of CCR5 but which is differentially accessible in the Δ32 vs wild-type sequence. Additionally, the sequences provided are designed to detect the mRNA expressed from CCR5. For probes to the DNA, probes directed to either strand of CCR5 may be used.

```
B1)  GCGAGGACTATCTTTAATGTATGGAAAATCTCGC       (SEQ ID NO: 39)

B2)  GCGAGGACTATCTTTAATGTATGGAAAATCTCGC       (SEQ ID NO: 40)

B3)  GCGAGGACTATCTTTAATGTATGGAAAATCTCGC       (SEQ ID NO: 41)

B4)  GCGAGGACTATCTTTAATGTATGGAAAATCTCGC       (SEQ ID NO: 42)

B5)  GCGAGGACTATCTTTAATGTATGGAAAATCTCGC       (SEQ ID NO: 43)

B6)  GCGAGGACTATCTTTAATGTATGGAAAATCTCGC       (SEQ ID NO: 44)

B7)  GCGAGGACTATCTTTAATGTATGGAAAATCTCGC       (SEQ ID NO: 45)

B8)  GCGAGGACTATCTTTAATGTATGGAAAATCTCGC       (SEQ ID NO: 46)

B9)  GCGAGGACTATCTTTAATGTATGGAAAATCTCGC       (SEQ ID NO: 47)

B10) GCGAGGACTATCTTTAATGTATGGAAAATCTCGC       (SEQ ID NO: 48)

B11) GCGAGGACTATCTTTAATGTATGGAAAATCTCGC       (SEQ ID NO: 49)

B12) GCGAGGACTATCTTTAATGTATGGAAAATCTCGC       (SEQ ID NO: 50)

B13) GCGAGGACTATCTTTAATGTATGGAAAATCTCGC       (SEQ ID NO: 51)

B14) GCGAGGACTATCTTTAATGTATGGAAAATCTCGC       (SEQ ID NO: 52)

B15) GCGAGGACTATCTTTaatgTATGGAAAATCTCGC       (SEQ ID NO: 53)

B16) GCGAGGACTATCTTTaatgTATGGAAAATCTCGC       (SEQ ID NO: 54)

B17) GCGAGGACTATCTTTaatgTATGGAAAATCTCGC       (SEQ ID NO: 55)

B18) GCGAGGACTATCtttAATGtatGGAAAATCTCGC       (SEQ ID NO: 56)

B19) GCGAGGACTATCtttAATGtAtGGAAAATCTCGC       (SEQ ID NO: 57)
```

Table 1 lists possible modifications that are used in effector oligonucleotides to disrupt CCR5 as well as in probes, regardless of how they are classified below, as they will also be tested in combination.

TABLE 1

| Duplex Stabilization |
| --- |
| BNA Bridged Nucleic Acids (BNA) |
| 2'-F—A, 2'-F—C, 2'F—Ac, 2'-F—G, 2'-F—U<br>2,6-Diaminopurine-2'-deoxyriboside<br>5-Methyl-2'-deoxycytidine<br>5-Propynyl-2'-deoxycytidine<br>5-Propynyl-2'-deoxyuridine<br>2,6-Diaminopurine-riboside<br>5-Methylcytidine<br>2'-Deoxyisoguanosine |

TABLE 1-continued

| Duplex Stabilization |
| --- |
| 2,6-Diaminopurine-2'-O-methylriboside<br>5-Methyl-2'-O-Methylcytidine<br>7-Deaza-8-aza-2'-deoxyadenosine<br>5-Methyl-2'-deoxyisocytidine |
| Nuclease Stability |
| Phosphorothioate DNA<br>2' O-Methyl RNA (Phosphodiester & Phosphorothioate)<br>Methylphosphonate<br>Bridged Nucleic acid (BNA)<br>Triplex Formation |
| Bridged Nucleic acid (BNA)<br>6-Thio-2'-deoxyguanosine<br>2'-Deoxypseudouridine<br>8-Amino-2'-deoxyadenosine<br>8-Amino-2'-deoxyguanosine |

Example 5—Inducing the Expression of CCR5 in Immune Stem Cells

This example describes methods to transiently induce the expression of CCR5 in immune stem cells without loss of the stem cell function.

The induction of expression of the CCR5 locus in immune stem cells is required for using the molecular beacon probes (e.g., Chromovert® probes) and conditions to detect cells comprising the Δ32 CCR5. Reagents and a treatment regimen that can induce the maximum transient expression of CCR5 in immune stem cells are selected by combinatorial testing of cytokines. The initial effective conditions that are identified are derivatized for further optimization.

The following parameters are used for selection and optimization: (i) one or a combination of two or more cytokines, (ii) concentration of each cytokine used, (iii) simultaneous or sequential treatment using the cytokines in the case where more than one is used, (iv) density of cells during treatment, (v) time duration of treatment, (vi) temperature shock or treatment step, and (vii) use of conditioned media or co-culturing of feeder cells. Similar parameters are used to test reagents (alone or in combination with cytokines) for activating or mobilizing immune stem cells.

Routine RT-PCR methods are then used to identify conditions that result in transient induction of CCR5 expression. The identified cells are then tested for the absence of any perturbation of stem cell function by applying methods to obtain the differentiated cells of the immune system from the treated immune stem cells and from untreated control immune stem cells and compare.

Example 6—Assessing the Extent of Genomic Modification

This example describes methods for testing the genomic integrity of treated immune stem cells using PCR-based approaches to determine if there is any unwanted genomic modification. The discussion below uses genome-wide sequencing approaches as a specific embodiment, but those skilled in the art will recognize, or be able to ascertain using no more than routine experimentation, other equivalents to the specific embodiment and methods discussed herein.

Compared to vector-based cell therapy methods (such as ZFN and RNAi methods), oligonucleotide-based methods do not necessitate the use of vectors, eliminating the risk of aberrant introduction of vector-encoded sequence into the genome of treated cells. Furthermore, oligonucleotide-based methods are reported to be highly inefficient, suggesting that off-target or unintended modification of the genome is unlikely or highly infrequent. Nevertheless, the extent of such unintended genomic modifications is assessed to ensure safety of the methods of this invention.

PCR-based methods to detect oligonucleotide-encoded sequence in the genome of treated cells are developed as a first line of testing. One such method is to amplify the digested genomic DNA of treated cells by using a primer based on the oligonucleotide sequence plus a mixture of other primers. Analysis of the amplified PCR products by gel electrophoresis in treated versus control cells is then used to detect any differences that could indicate the presence of oligonucleotide-encoded sequences in the genome. This method may not identify very rare genomic modifications; however, it is effective at detecting wide-spread and unintended modifications of the genome.

The whole genome of the treated cells that pass the first line of testing is then sequenced to detect any aberrant modification by the oligonucleotides. Analytical methods are developed and tested to ensure that all possible and small aberrant alterations of the genome caused by the oligonucleotides are reliably detected. For example, methods to assess the number of whole-genomes that must be sequenced for establishing with statistical certainty the level of risk that any aberrant modification of the genome may present are developed. Parameters such as the frequency and the likelihood of interrupting a coding or other functional sequence element within the genome are considered for establishing the statistical certainty.

Example 7—Identifying Immune Stem Cell Characteristics Correlating with Success for Use in the Methods of Invention This example describes methods to identify attributes of an individual's immune stem cells that may be correlated with effective operation of the methods of this invention.

Ideally, a cell therapy for HIV/AIDS should be equally applicable across different patients, regardless of sex, age, ethnicity or HIV/AIDS status. But due to the stem cell variability from different individuals, the success rate of the therapy may vary across different cohorts of patients. To determine whether the success of any aspect of the invention is correlated with a particular characteristic of immune stem cells, an aliquot of the stem cells used in each relevant step of the methods is evaluated and characterized using a number of tests. For example, the cells are characterized using RT-PCR and immunostaining to assess expression of key markers of immune stem cells and differentiated immune cells and compared.

This allows the identification of any patterns or characteristics that may be correlated with the effectiveness of these steps or the cells in these steps. The identification of any such characteristics can also inform and aid the development of methods that are more broadly applicable.

Example 8—Developing Methods for Cell Therapy

This example describes the sequence of steps and technologies implemented for the HIV/AIDS cell therapy developed by this invention. One embodiment of the invention employs the following steps and technologies: (i) immune stem cells are treated using the effector oligonucleotide and methods developed in Examples 1-3, (ii) expression of CCR5 are transiently induced in the treated cells using the reagents and methods of Example 5, (iii) the Chromovert® probes and conditions of Example 4 are used to detect and isolate the treated cells that comprise the Δ32 variant of CCR5; (iv) optionally, the attributes of any individuals or their immune stem cells correlating with successful outcomes of the invention as identified in Example 7 are used to prioritize the most promising immune stem cells for cell therapy of HIV/AIDS; and (v) isolate immune stem cells generated by the above steps that are (1) enriched for Δ32 mutation at one or both alleles, (2) viable, and (3) with retained stem cell function. As those skilled in the art will recognize, or be able to ascertain using no more than routine experimentation, other steps and technologies may be employed or substituted for any of the above steps to achieve the same function and results.

Optimal conditions to meet the end points of any one of the above steps could negatively impact meeting the end points of the other steps. For example, conditions that maximally induce CCR5 expression could negatively impact the preservation of the stem cell function of the cells that are isolated using the Chromovert® probes and relevant conditions. Consequently, the conditions for the induction of CCR5 expression and the Chromovert® process are adjusted such that sufficient CCR5 expression is induced while the stem cell function of the isolated cells is also preserved. The ranges of parameters and conditions used in either step are considered and further explored to achieve this balance.

Such conditions include the maximal yield of cells comprising the Δ32 variant of CCR5. High concentrations of oligonucleotides and powerful electroporation conditions to introduce the oligonucleotides into cells can achieve the greatest number of modified cells. However, these conditions may also increase the incidents of unintended off-target genome modifications. Further testing of the different conditions is performed to reach a balance between achieving the maximal efficiency at creating the cells comprising Δ32 CCR5 and keeping off-target genome modification at a minimum.

Such conditions also include the maximal yield of therapeutic cells. High cell sorting speeds during the Chromovert® process to detect and isolate cells treated to comprise Δ32 CCR5 may increase the yield of these cells; however, high speed cell sorting can lead to a decrease in cell viability and loss in stem cell function. Testing of different cell sorting speeds is performed to reach a balance between achieving maximal yield and retaining maximum stem cell viability and function.

Such conditions also include the isolation of cells enriched to uniquely comprise the Δ32 variant of CCR5. Chromovert® methods that rely on the use of multiple Chromovert® probes are used to enable detection of cells successfully treated to comprise the Δ32 variant of CCR5 at both chromosomal loci. By way of example, in addition to using one Chromovert® probe designed to detect the Δ32 variant of CCR5, simultaneous or sequential use of another Chromovert® probe designed to detect the wild-type variant of CCR5 is also used to select against cells that are reported as positive for wild-type CCR5. Employing such methods may require additional steps and manipulations of the cells. Testing of the different Chromovert® probes in combination with the possible additional steps is performed to achieve a balance between enriching optimally-modified cells and retaining the viability and functional capacity of the resulting isolated cells. This embodiment uses Chromovert® as an example, but those skilled in the art will recognize that other molecular beacon probes can be used in a similar way.

Example 9—Pre-Clinical Testing and Verification of the Cell Therapy

This example describes methods for testing the pre-clinical efficiency, efficacy and safety of the methods of the invention. The methods include in vitro cell-based assays and in vivo animal models that have been previously established and relied upon in pre-clinical testing.

The cell-based testing, which is performed first, includes tests designed to evaluate: (i) the percentage of cells treated with oligonucleotide comprising the Δ32 variant of CCR5 and the percentage comprising the Δ32 variant at both chromosomal loci, (ii) the efficiency of enrichment of cells comprising the Δ32 variant of CCR5 at one or both chromosomal loci developed by using the Chromovert® probes and conditions, (iii) the retention of stem cell function of the isolated cells following the steps of being treated with the oligonucleotides and going through the Chromovert® process, (iv) the extent and nature of aberrant modifications of the genome, if any, and (v) the resistance of the immune cells differentiated from the treated and selected immune stem cells to infection by HIV. As initial promising conditions are obtained in the context of these cell-based assays, a more thorough evaluation of pre-clinical efficacy and safety is then undertaken, including: (i) genome-wide sequencing to ascertain the extent and exact nature of aberrant modifications of the genome as a side-effect of the method, further including a statistical determination of the rate or frequency, (ii) the use of animal models to evaluate the retention of the stem cell function of the isolated cells in vivo, and (iii) the use of animal models to determine and characterize the resistance to HIV by the treated cells. The following tests 1-9 are examples of the testing methods that can be used.

Test 1: Cell-based evaluation of oligonucleotide-mediated methods to replicate the Δ32 variant of CCR5 in immune stem cells. PCR and sequencing methods to assess the efficiency of creating the Δ32 modification in immune stem cells using oligonucleotides are established. Methods for determining the percentage of treated cells that are modified at one or both chromosomal loci are developed and employed in the invention.

Test 2: Cell-based evaluation of the efficiency of Chromovert® probes and conditions to detect and isolate immune stem cells treated to comprise the Δ32 variant of CCR5. Cells treated with the optimized oligonucleotides to produce the Δ32 variant of CCR5 are subjected to cell sorting using Chromovert® reagents and conditions. See, for example, Larsson H. M., et al, *PLoS One.* 2012; 7(11):e49874. doi: 10.1371/journal.pone.0049874. Epub 2012 Nov. 27. The isolated cells are tested using genomic PCR and sequencing for detecting the level of enrichment of these cells compared to the input population. The viability of the sorted cells is then assessed using known method. The cells can be treated to transiently induce expression from the CCR5 locus prior to or during application of the Chromovert probes or process.

Test 3: Cell-based evaluation of the retention of stem cell function by the isolated immune stem cells treated to comprise the Δ32 variant of CCR5. Isolated immune stem cells treated to comprise the Δ32 variant of CCR5 are tested to evaluate the level to which they have retained their stem cell function. Conditions used to cause differentiation of mature immune cells from immune stem cells are applied and the resulting cells are characterized to determine whether all expected cells of the immune system have been generated.

Test 4: In vitro PCR-based evaluation of the extent of unintended modifications of the genome of treated cells. Methods to amplify genomic sequences that comprise oligonucleotide-encoded sequences are developed and used to approximate the level of aberrant off-target modifications of the genome of the treated cells.

Test 5: Cell-based evaluation of the resistance to infection by HIV of the differentiated mature immune cells obtained from the isolated stem cells. Isolated immune stem cells comprising the Δ32 variant of CCR5 according to the invention are grown in culture using standard methods to give rise to mature immune cells, including the immune CD4+ T-cell populations that are targeted and infected by HIV. The resulting cells are then infected with HIV. The resistance of these cells compared to control CD4+ T-cells is evaluated as a first measure to assess their resistance to infection by HIV.

Test 6: Whole-genome sequencing for a refined evaluation including a statistically-significant measure of the extent and nature of unintended modifications of the genome of the treated cells. After conditions that result in the lowest possible rate of aberrant and unintended off-target modifications of the genome are established, further testing including whole-genome sequencing is used for a more detailed examination of the extent and nature of such modification, if any. If necessary, the testing is expanded to obtain whole-genome sequencing data on a sufficient number of cells such that a statistically significant rate of off-target activity may be determined.

Test 7: In vivo animal studies for evaluation of the retention of stem cell function by the isolated immune stem cells treated to comprise the Δ32 variant of CCR5. Isolated immune stem cells comprising the Δ32 variant of CCR5 are introduced into nude mice following established methods used to generate human immune systems in this model. Analysis of the immune cells produced by the transformed mice is performed to evaluate the retention of stem cell function by the immune stem cells.

Test 8: In vivo animal studies for evaluating the resistance to infection by HIV of the differentiated mature immune cells obtained from the isolated stem cells. Upon success in Test 7, the transformed nude mice are exposed to HIV and then tested for infection by using established methods.

Test 9: Biological samples from patients are used and analyzed for the stem cells that have been modified for Δ32 CCR5 mutation and/or cells differentiated from stem cells that have been modified for Δ32 CCR5 mutation. The particular CCR5 mutation is analyzed to assess the effects of the stem cell therapy.

What is claimed is:

1. An effector oligonucleotide comprising a sequence selected from the group consisting of SEQ ID NO:5, SEQ ID NO:7, SEQ ID NO:9, and SEQ ID NO:11.

2. The effector oligonucleotide of claim 1, wherein the effector oligonucleotide comprises a mismatch in a human CCR5 sequence corresponding to a delta-32 CCR5 variant, wherein the effector oligonucleotide matches 40 to 200 bases of the human CCR5 sequence before the mismatch and matches 40 to 200 bases of the human CCR5 sequence after the mismatch.

3. The effector oligonucleotide of claim 1, wherein the effector oligonucleotide is a modified oligonucleotide.

4. The effector oligonucleotide of claim 3, wherein the effector oligonucleotide is modified to increase the strength of binding of the oligonucleotide to a target sequence or increase the stability of the oligonucleotide to degradation in buffers and in cells.

5. The effector oligonucleotide of claim 3, wherein modified oligonucleotide is a peptide nucleic acid (PNA) or comprises one or more bridged nucleotides (BNA).

6. A composition comprising the effector oligonucleotide of claim 1 and a pharmaceutically acceptable carrier.

7. A kit comprising an effector oligonucleotide according to claim 1.

8. The kit of claim 7 further comprising triplex-forming oligonucleotides or pseudocomplementary oligonucleotides.

9. The kit of claim 8 comprising triplex-forming oligonucleotides, wherein the triplex-forming oligonucleotides comprise a peptide nucleic acid (PNA).

10. The kit of claim 8 further comprising components for the detection of cells treated with the composition that comprise sequence encoded by the effector oligonucleotide.

11. The kit of claim 10, wherein the components for detection of cells comprise at least one molecular beacon probe.

12. The kit of claim 7, further comprising instructions for treating HIV infection.

13. The kit of claim 8, further comprising instructions for treating HIV infection.

* * * * *